(12) United States Patent
Akella et al.

(10) Patent No.: US 7,601,732 B2
(45) Date of Patent: Oct. 13, 2009

(54) CRYSTALLINE FORM OF 5(S)-(2-HYDROXYETHOXY)-20(S)-CAMPTOTHECIN

(75) Inventors: Venkateswarlu Akella, Hyderabad (IN); Shanavas Alikunju, Secunderabad (IN); Ajaya Kumar Reka, Hyderabad (IN); Ramesh Mullangi, Hyderabad (IN); Raju Sirisilla, Hyderabad (IN); Subrahmanyam Duvvuri, Hyderabad (IN); Sriram Rajagopal, Chennai (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 0 days.

(21) Appl. No.: 11/753,392

(22) Filed: May 24, 2007

(65) Prior Publication Data

US 2008/0076790 A1 Mar. 27, 2008

Related U.S. Application Data

(60) Provisional application No. 60/887,416, filed on Jan. 31, 2007.

(30) Foreign Application Priority Data

May 24, 2006 (IN) .......................... 897/CHE/2006

(51) Int. Cl.
*A61K 31/4745* (2006.01)
*C07D 491/22* (2006.01)

(52) U.S. Cl. ........................................ 514/283; 546/48
(58) Field of Classification Search ................. 514/283; 546/48

See application file for complete search history.

(56) References Cited

U.S. PATENT DOCUMENTS 6,177,439 B1 * 1/2001 Duvvuri et al. ............. 514/283

OTHER PUBLICATIONS

Wall et al., Plant Antitumor Agents. I. The Isolation and Structure of Camptothecin, a Novel Alkaloidal Leukemia and Tumor Inhibitor from Camptotheca acuminata, Journal of the American Chemical Society, (1966), pp. 3888-3890, Volume-Issue 88:16, ACS Publications, Washington, DC.

Poynter et al., Coulometric Karl Fischer titration simplifies water content testing, Oil & Gas Journal, (1994), pp. 1-5, Volume-Issue 92:15, Kam Controls Inc., Houston, TX.

Monks, et al., Feasibility of a High-Flux Anticancer Drug Screen Using a Diverse Panel of Cultured Human Tumor Cell Lines, Journal of the National Cancer Institute, (Jun. 5, 1991), pp. 757-766, Volume-Issue 83:11.

Stewart et al., Gefitinib Enhances the Antitumor Activity and Oral Bioavailability of Irinotecan in Mice, Cancer Research, Oct. 15, 2004), pp. 7491-7499, Volume-Issue 64:2.

Gorlick et al., Biology of Childhood Osteogenic Sarcoma and Potential Targets for Therapeutic Development: Meeting Summary, Clinical Cancer Research, (Nov. 15, 2003), pp. 5442-5453, vol. 9.

Benet et al., Appendix ll Design and Optimization of Dosage Regimens; Pharmacokinetic Data, Goodman & Goodman's the Pharmacological Basis of Therapeutics, Ninth Edition, pp. 1707-1711., 1996.

Alfonso R. Gennaro, Remington: The Science and Practice of Pharmacy, 20th Edition, (Lippincott, Williams and Wilkins), 2000.

John E. Hoover, Remington's Pharmaceutical Sciences, Mack Publishing Co., Easton Pennsylvania, Fifteenth Edition, 1975.

Liberman et al., Pharmaceutical Dosage Forms: Tablets vols. 1-3, Marcel Decker, New York, N.Y., 1980.

Kibbe et al., Handbook of Pharmaceutical Excipients, Third Edition, American Pharmaceutical Association, Washington, D.C., 1999.

* cited by examiner

*Primary Examiner*—Charanjit S Aulakh
(74) *Attorney, Agent, or Firm*—Nelson Mullins Riley & Scarborough, LLP

(57) ABSTRACT

A crystalline form of 5(S)-(2'-hydroxyethoxy)-20(S)-camptothecin diastereoisomer of 5(RS)-(2'-hydroxyethoxy)-20(S)-camptothecin is described that is characterized by having an X-ray powder diffraction pattern comprising one or more peak intensities expressed in degrees 2θ that are selected from the group consisting of 7.2±0.1, 9.4±0.1, 11.02±0.1, 12.00±0.1, 14.54±0.1, 15.2±0.1, 18.92±0.1, 21.86±0.1, 22.74±0.1 and 26.42±0.1. Methods of making and using the compound are also described.

36 Claims, 13 Drawing Sheets

Top: Experimental X-Ray Diffraction Pattern of powder
Bottom: Simulated X-Ray Diffraction Pattern of single crystal

CRYSTALLINE FORM OF 5(S)-(2-HYDROXYETHOXY)-20(S)-CAMPTOTHECIN

CROSS REFERENCE TO RELATED PATENTS AND PATENT APPLICATIONS

The subject matter of the present invention is related to U.S. Pat. No. 6,177,439, issued 23 Jan. 2001, and to copending and commonly owned U.S. Non-provisional patent application having the title: 5(S)-(2'-hydroxyethoxy)-20(S)-camptothecin And Its Preparation and Use For The Treatment of Cancer, which was filed on the same date as the present application, each of which is incorporated herein by reference in its entirety.

The present application is a non-provisional of and claims the benefit of India provisional application No. 897/CHE/2006, filed 24 May 2006, and to U.S. Provisional Application No. 60/887,416, filed 31 Jan. 2007, each of which is relied on herein and incorporated herein by reference in its entirety.

BACKGROUND OF THE INVENTION (1) Field of the Invention

The present invention generally relates to a crystalline form of 5(S)-(2'-hydroxyethoxy)-20(S)-camptothecin, to methods for its preparation, and to methods and compositions for its use.

(2) Description of the Related Art

Camptothecin (CPT) is a pentacyclic plant alkaloid first isolated from the Chinese tree *Camptotheca acuminate* by Wall et al., *J. Am. Chem. Soc.*, 88: 3888 (1966). The structure of camptothecin is shown in formula I:

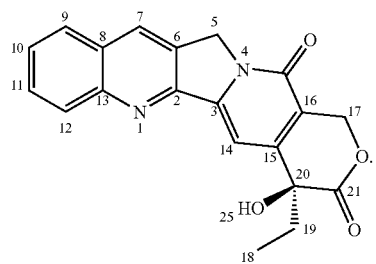

(I)

Without modification, camptothecin is highly lipophilic and poorly water soluble. Early clinical trials using sodium camptothecin solubilized by sodium hydroxide in water showed that the compound had antineoplastic activity, and further research demonstrated that the activity was due to the action of the compound as an inhibitor of DNA topoisomerase I. However, the therapeutic potential of camptothecin has thus far failed to be fully realized on account of toxicity problems and limited water solubility.

Attempts to provide improved properties for this compound have included the synthesis and testing of numerous analogues of camptothecin. For example, U.S. Pat. No. 5,004,758 describes water soluble camptothecin analogues, U.S. Pat. No. 5,734,056 describes camptothecin analogues. Topotecan, an analogue of camptothecin, is discussed in U.S. Pat. No. 5,004,758, and U.S. Patent Publication US 2007/0105885.

Various Carbon-5 substituted analogues of 20(S)-camptothecin are described in U.S. Pat. No. 6,177,439. One such analogue, 5(RS)-(2'-hydroxyethoxy)-20(S)-camptothecin has the structure shown in formula II:

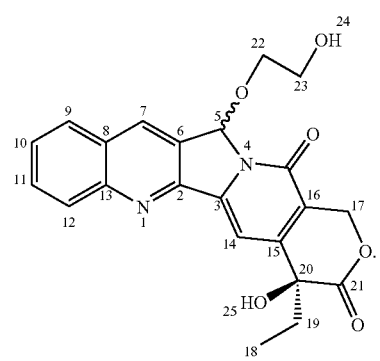

(II)

The U.S. Pat. No. 6,177,439 patent discloses processes for the preparation of the diastereoisomeric mixture of this analogue—referred to herein as 5(RS)-(2'-hydroxyethoxy)-20(S)-camptothecin, or as 5-(2'-hydroxyethoxy)-20(S)-camptothecin.

5(RS)-(2'-hydroxyethoxy)-20(S)-camptothecin is a 5-alkoxy substituted 20(S)-camptothecin analog having a penta cyclic structure. It has chiral centers at Carbon-5 and Carbon-20 positions. The Carbon-20 chiral center corresponds to the natural S-configuration. However, the Carbon-5 substitution represents both R and S diastereoisomers in an approximately equal ratio. The molecular formula of 5(RS)-(2'-hydroxyethoxy)-20(S)-camptothecin is $C_{22}H_{20}N_2O_6$. The compound has a molecular weight of 408.41 g/mole and a melting point of 190° C. The diastereoisomeric mixture 5(RS)-(2'-hydroxyethoxy)-20(S)-camptothecin, or as 5-(2'-hydroxyethoxy)-20(S)-camptothecin has poor water solubility.

The 5(S)-(2'-hydroxyethoxy)-20(S)-camptothecin diastereomer of 5(RS)-(2'-hydroxyethoxy)-20(S)-camptothecin is described chemically as 5(S)-(2-hydroxyethoxy)-20(S)-camptotheci n, whereas the 5(R)-(2'-hydroxyethoxy)-20(S)-camptothecin diastereomer of 5(RS)-(2'-hydroxyethoxy)-20(S)-camptothecin is described chemically as 5(R)-(2'-hydroxyethoxy)-20(S)-camptothecin. 5(S)-(2'-hydroxyethoxy)-20(S)-camptothecin is also chemically described as 4-(S)-Ethyl-4-hydroxy-12(S)-(2-hydroxyethoxy)-1,12-dihydro-4H-2-oxa-6,12a-diazadibenzo[b,h]fluorene-3,13-dione, which has the following chemical structure shown in formula III:

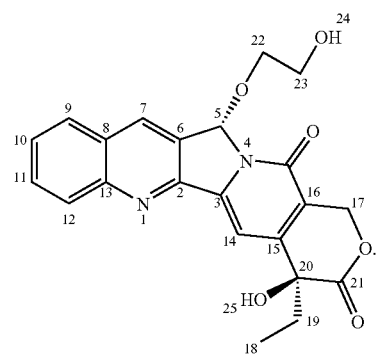

(III)

The 5(R)-(2'-hydroxyethoxy)-20(S)-camptothecin diastereoisomer has the chemical structure shown in formula IV:

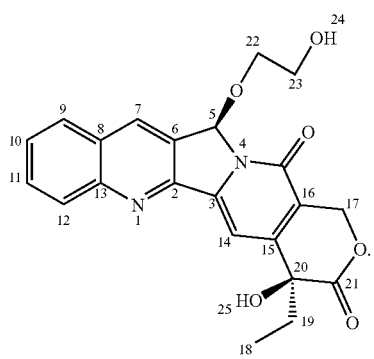

(IV)

Generally speaking, isomers that are enantiomers have, when present in a symmetric environment, identical chemical and physical properties except for their ability to rotate plane-polarized light by equal amounts, but in opposite directions. On the other hand, isomers that are diastereomers (or diastereoisomers) are stereoisomers but are not enantiomers. Diastereomers can, and most often do, have different physical properties and different reactivity. In another definition diastereomers are pairs of isomers that have opposite configurations at one or more of the chiral centers but are not mirror images of each other.

It is well known that different solid-state forms of a compound can have different physical properties. In a pharmaceutical compound, such differences can have a significant effect on the success of commercial versions of the compound. For example, a compound having different solid phase morphology can have different packing properties such as molar volume, density and hygroscopicity, different thermodynamic properties such as melting temperature and solubility, different kinetic properties such as dissolution rate and stability (including stability at ambient conditions, especially to moisture and under storage conditions), different surface properties such as surface area, wettability, interfacial tension and shape, different mechanical properties such as hardness, tensile strength, compactibility, handling, flow and blend, and/or different filtration properties. Such differences in physical properties can affect how a pharmaceutical compound is made, processed, formulated or administered.

Another important solid state property of a pharmaceutical compound is its rate of dissolution in aqueous fluid. The rate of dissolution of an active ingredient in a patient's body fluid can have therapeutic consequences since it imposes an upper limit on the rate at which an orally-administered active ingredient can reach the patient's bloodstream. Thus, the rate of dissolution can have a significant effect on the therapeutic efficacy of the administered drug.

Typically, the rate of dissolution of a pharmaceutical compound depends upon its stable crystalline form. Also, this property of the pharmaceutical compound is considered as an important feature in formulating syrups, elixirs and other liquid medicaments. The solid state form of a compound may also affect its behavior on compaction and its storage stability.

Thus, it is clear from the foregoing that it would be desirable to provide the active 5(S)-(2'-hydroxyethoxy)-20(S)-camptothecin pharmaceutical ingredient of 5(RS)-(2'-hydroxyethoxy)-20(S)-camptothecin in a stable crystalline form having desired bulk handling and dissolution properties.

SUMMARY OF THE INVENTION

Briefly, therefore the present invention is directed to a novel 5(S)-(2'-hydroxyethoxy)-20(S)-camptothecin in the crystalline form that is characterized by having an X-ray powder diffraction pattern comprising one or more peak intensities expressed in degrees 2θ that are selected from the group consisting of 7.2±0.1, 9.4±0.1, 11.02±0.1, 12.00±0.1, 14.54±0.1, 15.2±0.1, 18.92±0.1, 21.86±0.1, 22.74±0.1 and 26.42±0.1.

The present invention is also directed to a novel pharmaceutical composition comprising the crystalline 5(S)-(2'-hydroxyethoxy)-20(S)-camptothecin as described above and a pharmaceutically acceptable carrier.

The present invention is also directed to a novel method of using crystalline 5(S)-(2'-hydroxyethoxy)-20(S)-camptothecin for the production of a pharmaceutical composition, the method comprising intermixing the crystalline 5(S)-(2'-hydroxyethoxy)-20(S)-camptothecin described above with a pharmaceutically acceptable carrier.

The present invention is also directed to a novel method of making the crystalline 5(S)-(2'-hydroxyethoxy)-20(S)-camptothecin described above, the method comprising the steps:

a) intermixing 5(RS)-(2'-hydroxyethoxy)-20(S)-camptothecin with a solvent selected from n-butanol or tetrahydrofuran;

b) refluxing the mixture for a period of from about 1 to about 4 hours;

c) cooling the mixture to a temperature of from about 40° C. to about 50° C.; and d) separating solid 5(S)-(2'-hydroxyethoxy)-20(S)-camptothecin from the mixture.

The present invention is also directed to a novel method of using crystalline 5(S)-(2'-hydroxyethoxy)-20(S)-camptothecin to treat cancer in a subject, the method comprising administering to the subject an effective amount of the crystalline 5(S)-(2'-hydroxyethoxy)-20(S)-camptothecin described above.

Among the several advantages found to be achieved by the present invention, therefore, may be noted the provision of the active 5(S)-(2'-hydroxyethoxy)-20(S)-camptothecin pharmaceutical ingredient of 5(RS)-(2'-hydroxyethoxy)-20-(S)-camptothecin in a stable crystalline form having desired bulk handling and dissolution properties.

DETAILED DESCRIPTION OF THE PREFERRED EMBODIMENTS

Figure 1:
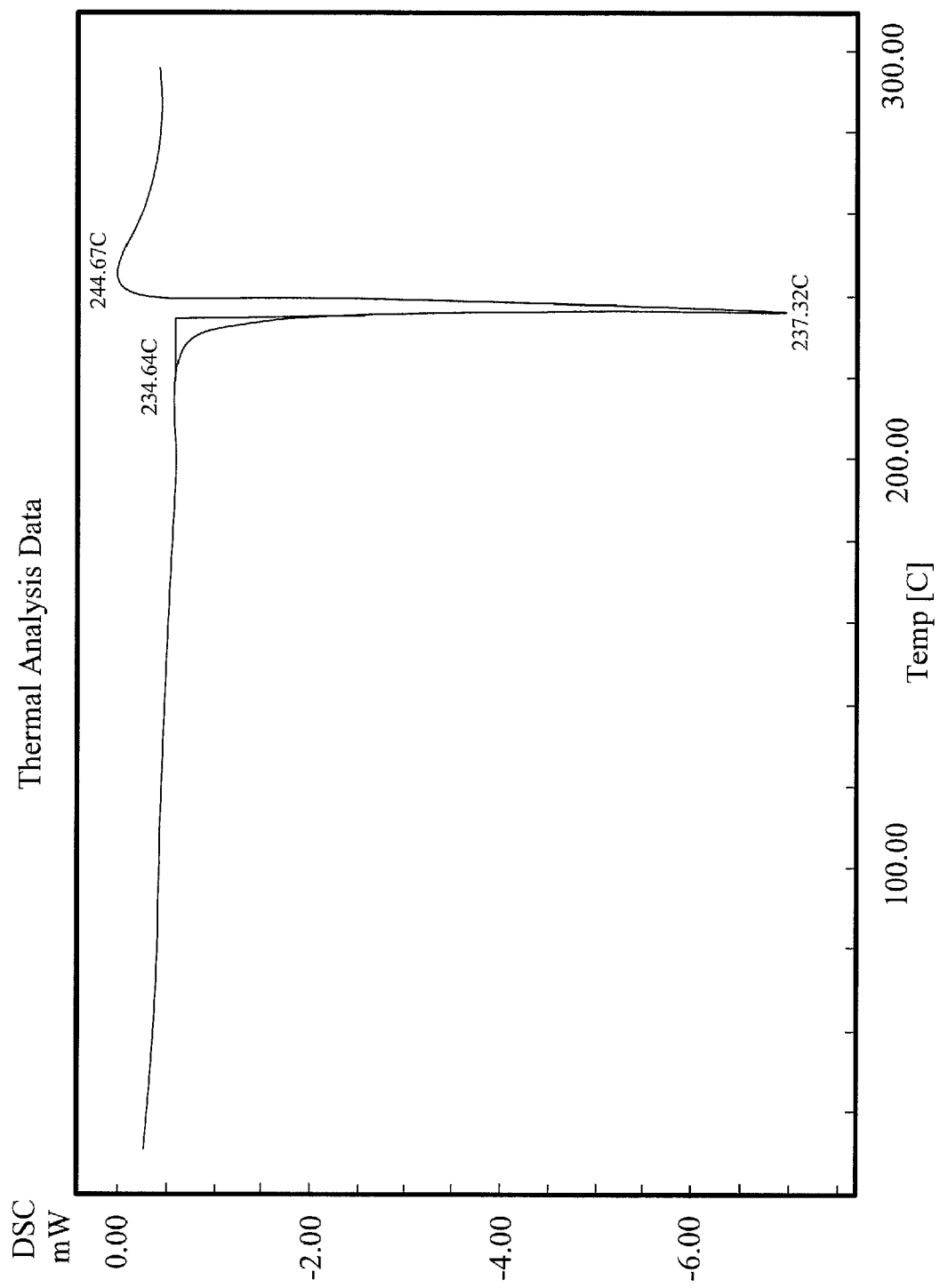
FIG. 1 shows a differential scanning calorimetry (DSC) thermogram of a solid form embodiment of 5(S)-(2'-hydroxyethoxy)-20(S)-camptothecin of the present invention.

The present invention relates to the solid state physical properties of 5(S)-(2'-hydroxyethoxy)-20(S)-camptothecin and to the utility of a crystalline form in the formulation and activity of pharmaceuticals. In accordance with the present invention, it has been discovered that a novel crystalline form of the 5(S)-(2'-hydroxyethoxy)-20(S)-camptothecin diastereomer of 5(RS)-(2'-hydroxyethoxy)-20(S)-camptothecin provides advantages over the racemic form of the compound and also over the 5(R)-(2'-hydroxyethoxy)-20(S)-camptothecin form of the compound. Moreover, a crystalline form that is described herein as one embodiment of the invention also provides advantages over other solid-state forms in making, processing, formulating and/or administering the compound.

In other embodiments, the present crystalline form of 5(S)-(2'-hydroxyethoxy)-20(S)-camptothecin can be anhydrous. The present crystalline form of 5(S)-(2'-hydroxyethoxy)-20(S)-camptothecin can be non-hygroscopic and has a high degree of physical stability and demonstrates acceptable solid-state properties at normal room temperature environments. Moreover, the present crystalline form composition is useful for the treatment and/or prophylaxis of cancerous diseases and disorders.

The present invention also includes methods for the preparation of the novel crystalline form of 5(S)-(2'-hydroxyethoxy)-20(S)-camptothecin.

The invention is also directed to a pharmaceutical composition comprising the novel crystalline form of 5(S)-(2'-hydroxyethoxy)-20(S)-camptothecin and a pharmaceutically acceptable carrier, and various embodiments of the present composition as adapted for administration via oral, injection, inhalation, eye drops, intravenous, and other pathways, as discussed below.

In another embodiment, the crystalline form of 5(S)-(2'-hydroxyethoxy)-20(S)-camptothecin has a water content that is less than about 1% w/w, or less than about 0.5% w/w, or even less than about 0.25% w/w when measured by coulometric Karl Fischer (KF) titration (See, e.g., Poynter, W. G. and R. J. Barrios, *Oil and Gas Journal*, 92:15 (1994).

The selection of a solid state form of 5(S)-(2'-hydroxyethoxy)-20(S)-camptothecin that is physically stable during a manufacturing process, such as milling to obtain a material with reduced particle size and increased surface area, can avoid need for special processing conditions and the increased costs generally associated with such special processing conditions. Similarly, the selection of a solid state form of 5(S)-(2'-hydroxyethoxy)-20(S)-camptothecin that is physically stable over a range of storage conditions can help avoid polymorphic or other degradative changes in the compound that can lead to product loss or deterioration of product efficacy. Therefore, the selection of a solid state form of 5(S)-(2'-hydroxyethoxy)-20(S)-camptothecin having greater physical stability provides a meaningful advantage.

In one embodiment, the present crystalline form of 5(S)-CPT has overall phase purity of over about 90%, or over about 95%, or even over about 97%, or over about 98%, or over about 99%.

A new crystalline form of 5(S)-CPT is described herein. In certain embodiments, the crystalline 5(S)-CPT is substantially free of 5(R)-(2'-hydroxyethoxy)-20(S)-camptothecin. When the present crystalline 5(S)-CPT is described as being substantially free of 5(R)-CPT, it is meant that the amount of 5(R)-CPT in the CPT is less than about 2% w/w of the total amount of CPT; or less than about 1.5% w/w; or less than about 1% w/w; or less than about 0.5% w/w; or even less than 0.1% w/w.

The present crystalline 5(S)-CPT is advantageous because it is non-hygroscopic, it is stable, it exists in a crystalline form, and can exist in an anhydrous form. It is easier to handle and store the present crystalline 5(S)-CPT as compared to the diastereoisomeric mixture 5(RS)-CPT because of its increased physical stability.

Additional aspects and embodiments of the invention are discussed throughout the specification of this application.

As used herein, the term "DSC" refers to differential scanning calorimetry.

As used herein, the term "XRPD" refers to X-ray powder diffraction.

As used herein in reference to nuclear magnetic resonance ($^1$H NMR), the symbol "δ" refers to a $^1$H NMR chemical shift; the abbreviation "d" refers to a doublet $^1$H NMR peak; the abbreviation "m" refers to a multiplet $^1$H NMR; the abbreviation "q" refers to a quartet $^1$H NMR peak; the abbreviation "s" refers to a singlet $^1$H NMR peak; the abbreviation "t" refers to a triplet $^1$H NMR peak.

As used herein in reference to camptothecin, the terms "Carbon-5 position" refer to the carbon atom present at the 5$^{th}$ position of the chemical structure of 5(S)-(2-hydroxyethoxy)-20(S)-camptothecin as shown in formula II above, and the terms "Carbon-20 position" refer to the carbon atom present at the 20$^{th}$ position of the chemical structure of 5(S)-(2-hydroxyethoxy)-20(S)-camptothecin as shown in formula II.

As used herein, throughout the present description "5(S)-CPT" refers to "5(S)-(2'-hydroxyethoxy)-20(S)-camptothecin", which is chemically known as "4(S)-Ethyl-4-hydroxy-12-(S)-(2-hydroxyethoxy)-1,12-dihydro-4H-2-oxa-6,12a-diaza-dibenzo[b,h]fluorine-3,13-dione".

As used herein, throughout the present description "5(R)-CPT" refers to "5(R)-(2'-hydroxyethoxy)-20(S)-camptothecin", which is chemically known as "4(S)-Ethyl-4-hydroxy-12-(R)-(2-hydroxyethoxy)-1,12-dihydro-4H-2-oxa-6,12a-diaza-dibenzo[b,h]fluorine-3,13-dione".

As used herein, throughout the present description "5(RS)-CPT" refers to "5(RS)-(2'-hydroxyethoxy)-20(S)-camptothecin" or "5-(2'-hydroxyethoxy)-20(S)-camptothecin", which is chemically known as "4(S)-Ethyl-4-hydroxy-12-(RS)-(2-hydroxyethoxy)-1,12-dihydro-4H-2-oxa-6,12a-diaza-dibenzo[b,h]fluorine-3,13-dione".

As used herein, the term "composition" refers to an article of manufacture which results from the mixing or combining of more than one element or ingredient.

As used herein, the term "single crystal", also called monocrystal, is meant to refer to a crystalline solid in which the crystal lattice of the entire sample is continuous and unbroken to the edges of the sample, with no grain boundaries.

As used herein in reference to 5(S)-(2'-hydroxyethoxy)-20(S)-camptothecin, the term "crystalline form" refers to a solid-state form wherein the 5(S)-(2'-hydroxyethoxy)-20(S)-camptothecin molecules are arranged to form a distinguishable crystal lattice (i) comprising distinguishable unit cells, and (ii) yielding diffraction peaks when subjected to X-ray radiation.

The term "phase purity", as used herein, refers to purity with respect to other solid state forms of 5(S)-(2'-hydroxyethoxy)-20(S)-camptothecin and does not necessarily imply a high degree of chemical purity with respect to other components.

As used herein, the term "about", when referring to a measured quantity, refers to the normal variation in that measured quantity as would be expected by the skilled person making the measurement and exercising a level of care commensurate with the objective of measurement and the precision of the measuring equipment.

As used herein, the term "anhydrous" means a substance is substantially free of water, and the substance can contain less than about 1.0% water w/w, and the substance can contain even less than about 0.5% water w/w. As used herein, the terms "anhydrous" and "anhydrate" are used interchangeably.

The term "non-hygroscopic", as used herein with reference to a material, means that the material is one which does not attracts moisture from the atmosphere under normal room temperature, pressure and humidity conditions.

As used herein, the terms "pharmaceutically acceptable carrier" refer to a carrier that is compatible with the other ingredients of the composition and is not deleterious to the subject. Such carriers may be pharmaceutically acceptable material, composition or vehicle, such as a liquid or solid filler, diluent, excipient, solvent or encapsulating material, involved in carrying or transporting a chemical agent. As will be discussed in more detail below, the preferred composition depends on the method of administration.

As used herein, the terms "therapeutically effective amount" refer to that amount of drug or pharmaceutical agent that will elicit the biological or medical response of a tissue, system or animal that is being sought by a researcher or clinician.

The term "treatment" (and corresponding terms "treat" and "treating"), as used herein, refer to palliative, restorative, and preventative treatment of a subject.

The term "prophylaxis', as used herein, refers to a measure taken to maintain health and prevent the spread of disease in a subject.

As used herein, the following terms/symbols have the meaning shown:
'kg' refers to 'kilograms'
'mg' refers to 'milligrams'.
'μl' refers to 'micro liters'
'μg' refers to 'micrograms'
'"KBr"' refers to 'potassium bromide'
'DMSO' refers to 'dimethylsulfoxide'
Characterization of Crystalline 5(S)-CPT:
Measurement of Water Content by Karl Fisher Titration:
The water content of crystalline 5(S)-CPT was measured by Mettler® DL 31 KF apparatus by using Karl Fischer reagent. A weighed quantity of crystalline 5(S)-CPT was transferred into a titration vessel of a Karl Fischer apparatus containing about 40 ml of previously neutralized methanol. The sample was dissolved with stirring, and was titrated with Karl Fisher Reagent to the end point under vigorous stirring. Water content was calculated as:

$$\% \text{ water content in w/w} = \frac{\text{Titer value} \times KF \text{ factor} \times 100}{\text{Sample weight in g} \times 1000}$$

No change in water content was observed during accelerated stability conditions at 40° C.±2° C./765% RH±5% RH for 6 months as measured by Karl Fisher analysis and was found to be non-hygroscopic. The product is stable in 6 months accelerated conditions.

Differential Scanning Calorimetry (DSC) Analysis:
DSC analysis of crystalline 5(S)-CPT was performed using a Shimadzu® DSC-50 calorimeter. Samples were placed in an aluminum pan, the weight accurately recorded and the pan covered with a lid and left unclamped. Each sample was equilibrated and heated at a rate of 5° C./minute under nitrogen atmosphere. The temperature of the melting endothermic peak was reported as the melting point. The data from DSC analyses was dependent on several factors, including the rate of heating, the purity of the sample, crystal size, and sample size. The present crystalline 5(S)-CPT is also characterized by a single melting endotherm peak at a temperature between about 234° C. and 238° C., or between about 234° C. and 236° C. as measured by DSC and shown in FIG. 1.

X-Ray Powder Diffraction (XRPD):
The crystal structures of 5(S)-CPT were analyzed using X-ray powder diffraction ("XRPD"). The X-ray powder diffraction spectra were determined using a Rigaku D/Maz 2200 diffractometer equipped with horizontal goniometer in θ/2θ geometry. The X-ray tube used was a Cu K-alpha with a wavelength of 1.5418 Å at 50 KV and 34 mA. The divergence and scattering slits were set at 0.5° and the receiving slit set at 0.15 mm. Diffracted radiation was detected by scintillation counter detection, θ to 2θ continuous scan at 3 degrees/minute from 3 to 45 degrees.

Figure 2:
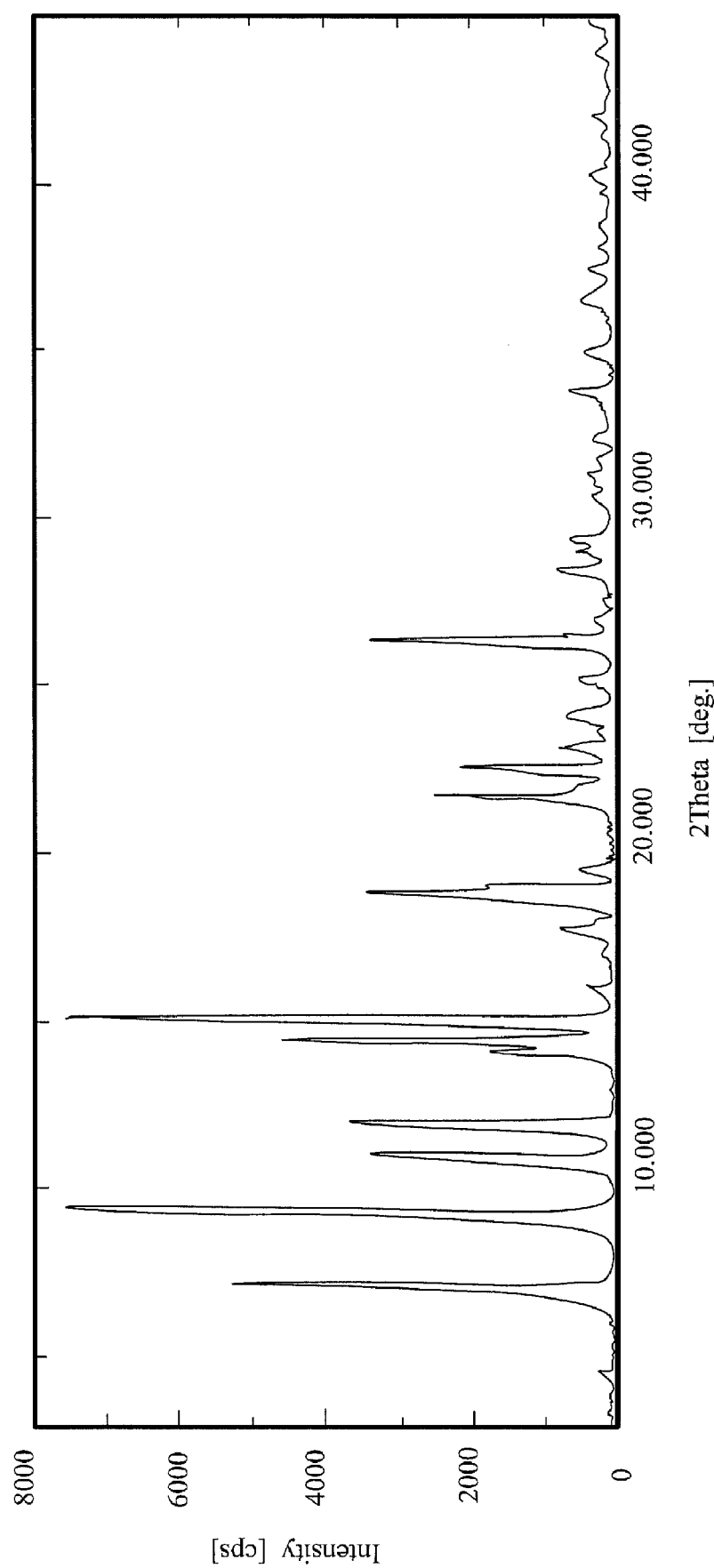
FIG. 2 shows a X-ray powder diffraction (XRPD) pattern of a solid form embodiment of 5(S)-(2'-hydroxyethoxy)-20 (S)-camptothecin of the present invention.

An illustrative XRPD pattern for crystalline 5(S)-CPT is shown in FIG. 2. Table 1 lists the corresponding main diffraction peaks in terms of 2θ values and intensities for crystalline 5(S)-CPT.

TABLE 1

Characteristic XRPD peaks of crystalline 5(S)-CPT.

| 2 Theta (2θ) | Percentage relative intensity (I/I$_o$) |
|---|---|
| 7.2 | 76 |
| 9.4 | 93 |
| 11.02 | 52 |
| 12.00 | 51 |
| 14.54 | 65 |
| 15.20 | 100 |
| 18.92 | 45 |
| 21.86 | 39 |
| 22.74 | 34 |
| 26.42 | 54 |

It should be recognized that in a mixture of the crystalline 5(S)-CPT with another phase not all the peaks listed in Table 1 may be apparent in the mixture's powder diffraction pattern.

Potential for Isomerism and Identification of Stereochemistry:
The sample of 5(S)-CPT was submitted for single crystal diffraction studies with an objective to determining the absolute stereochemistry at the Carbon-5 position of 5(S)-CPT. Crystals suitable for X-ray diffraction study were grown from dimethylsulfoxide. 5(S)-CPT crystallizes in monoclinic space group P21 with unit cell parameters a=6.308(1)Å, b=15.924(3)Å, c=18.771(4)Å, β=95.519(5)Å; V=1876.8(7) Å3 and Z=4. The X-ray intensity data were collected on Rigaku AFC-7S single crystal diffractometer using graphite monochromatic MoKa radiation (λ=0.7107 Å) on a CCD area-detector. The structure was solved with direct methods (SIR92 software) and refined using least squares procedures. The final R(Rw) is 0.041 (0.044) for 3713 observed reflections.

Figure 3:
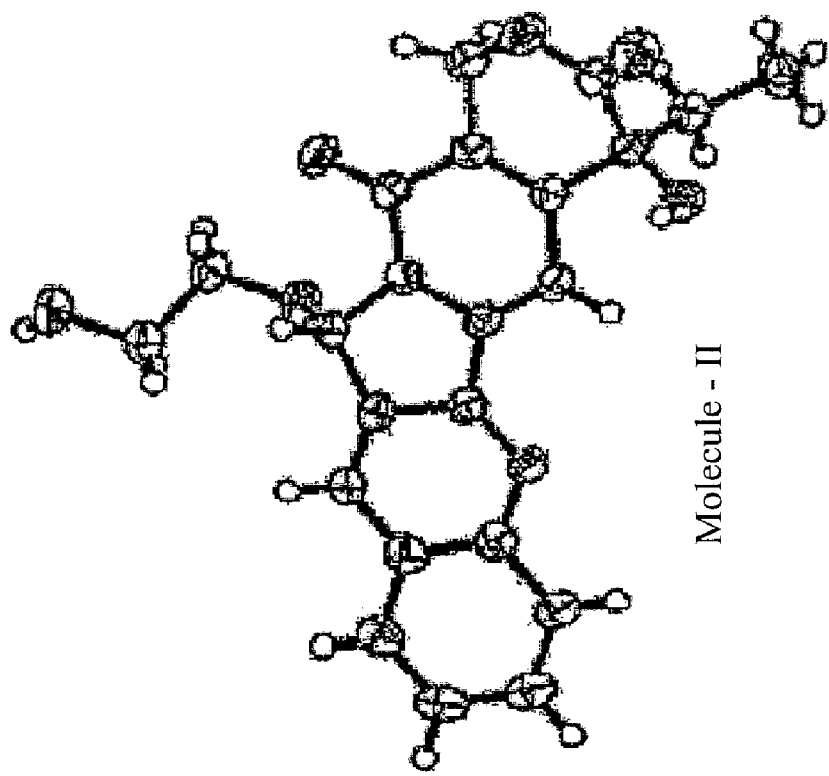
FIG. 3 illustrates the spatial relationship of two independent molecules I & II of 5(S)-(2'-hydroxyethoxy)-20(S)-camptothecin in a unit cell of a solid form of a compound of the present invention.
Figure 3:
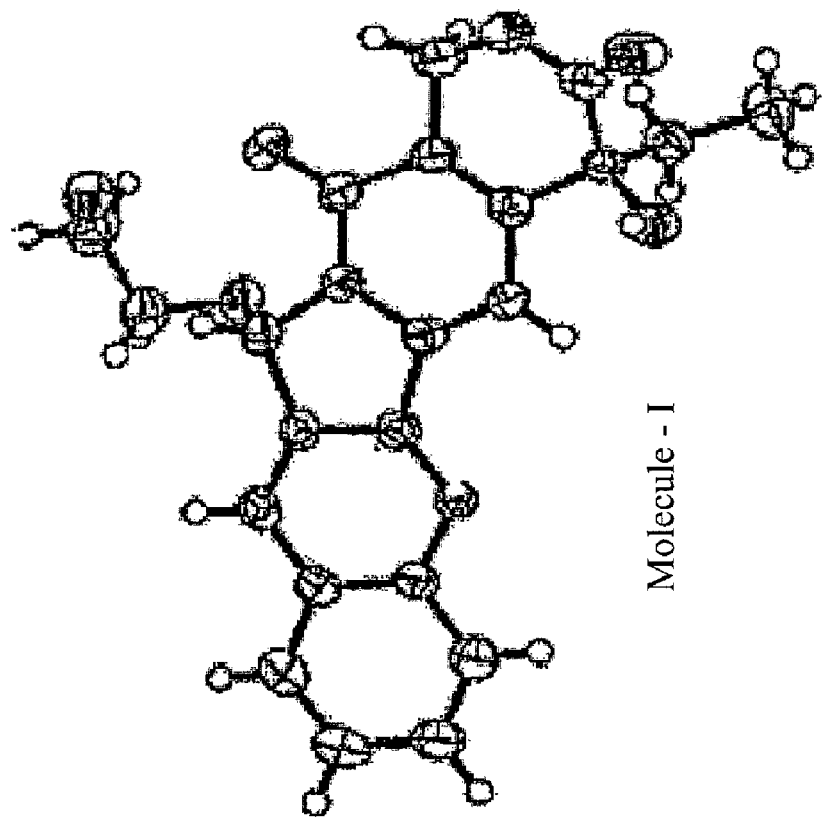

The two independent molecules I & II (FIG. 3) in the unit cell differ in the conformation of the side chain at Carbon-5 position of 5(S)-CPT.

Based on the known configuration at Carbon-20 position to be S stereo centre, the absolute stereochemistry at Carbon-5 position is determined to be S stereo centre.

Figure 4:
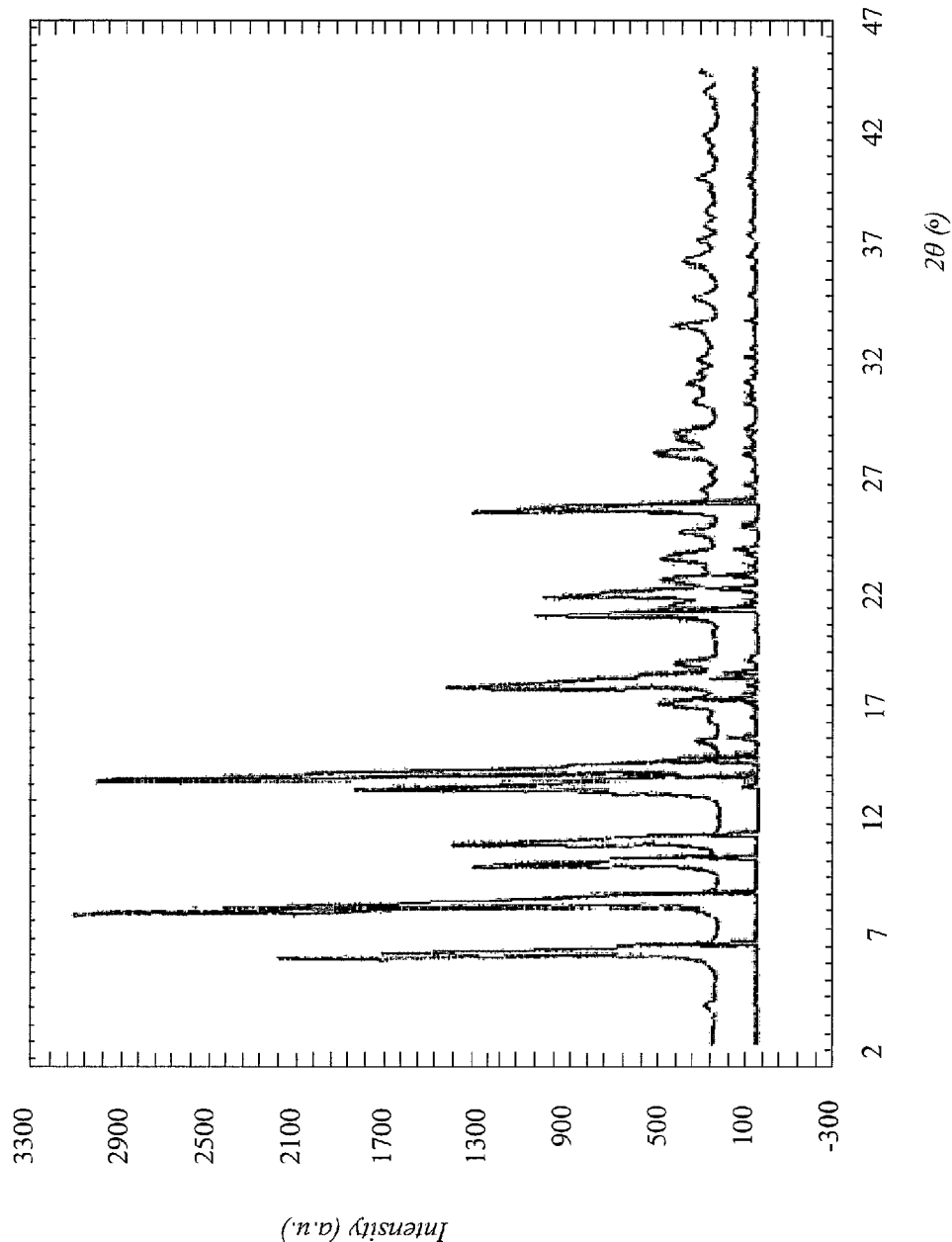
FIG. 4 shows a comparison of a simulated X-ray diffraction pattern of a single crystal of 5(S)-(2'-hydroxyethoxy)-20(S)-camptothecin with an experimental powder X-ray diffraction pattern of an embodiment of a crystalline form of 5(S)-(2'-hydroxyethoxy)-20(S)-camptothecin of the present invention.

The simulated powder X-ray pattern from single crystal X-ray diffraction and data of the experimental powder X-ray diffraction match well with each other (FIG. 4).

Fourier-Transform Infrared (FT-IR) Spectrometry:

Crystalline 5(S)-CPT was also characterized by Fourier Transform Infra Red (FT-IR) spectra and recorded in solid state as KBr dispersion. A Perkin-Elmer® 1650 Fourier Transform Infra Red spectrophotometer was used for characterization. Experimental error, unless otherwise noted, was ±2 cm$^{-1}$.

Crystalline 5(S)-CPT was shown to have infrared spectrum comprising absorption bands at about 3271, 2927, 1743, 1669, 1607, 1504, 1465, 1405, 1342, 1225, 1158, 1188, 1080, 1120, 1043, 992, 893, 838, 796, 772, and 659 cm$^{-1}$. The infrared spectrum is substantially in accordance with that shown in FIG. 5.

Figure 6:
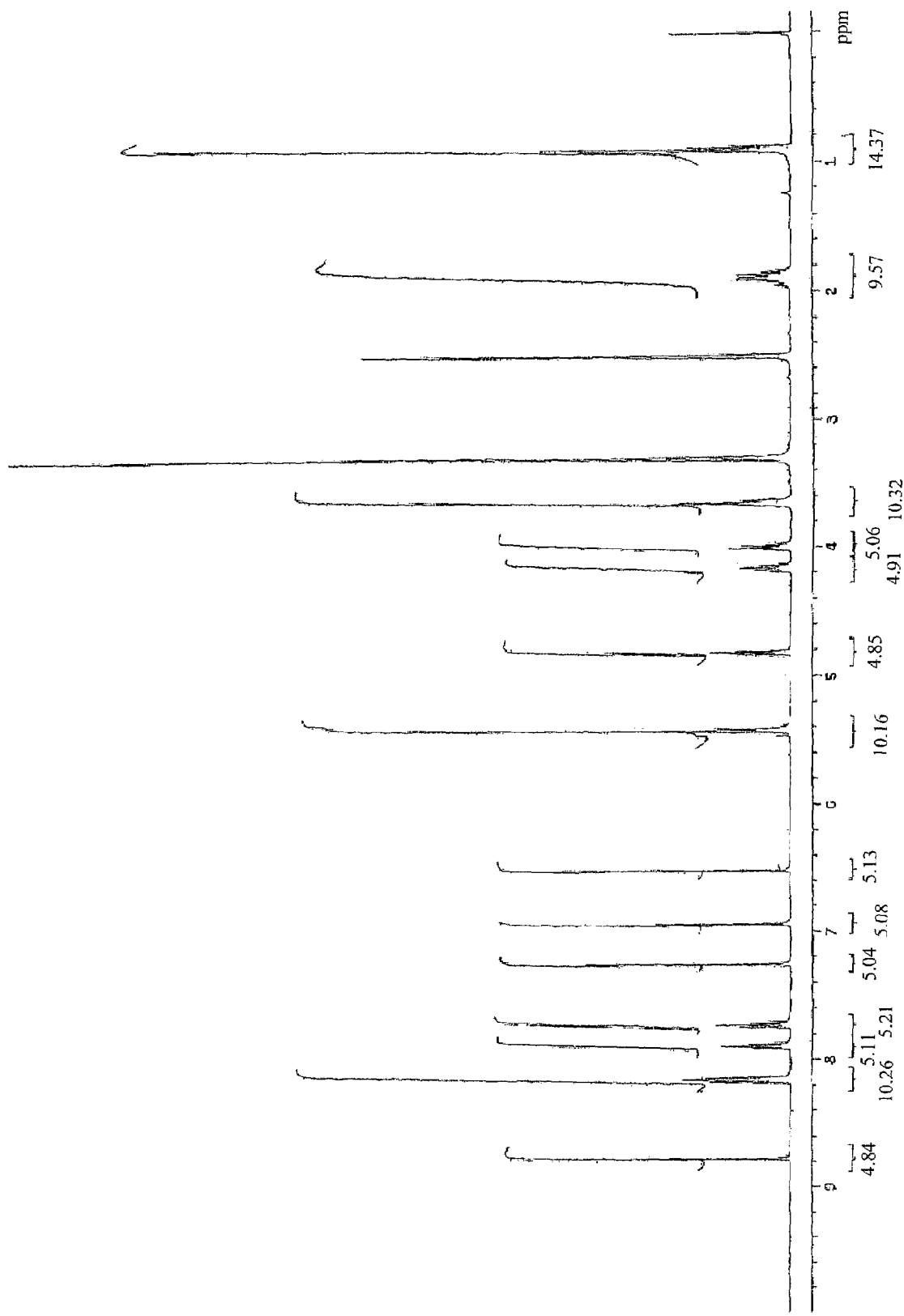
FIG. 6 shows a proton nuclear magnetic resonance ($^1$H NMR) spectrum of 5(S)-(2'-hydroxyethoxy)-20(S)-camptothecin in DMSO-d6.
Figure 7:
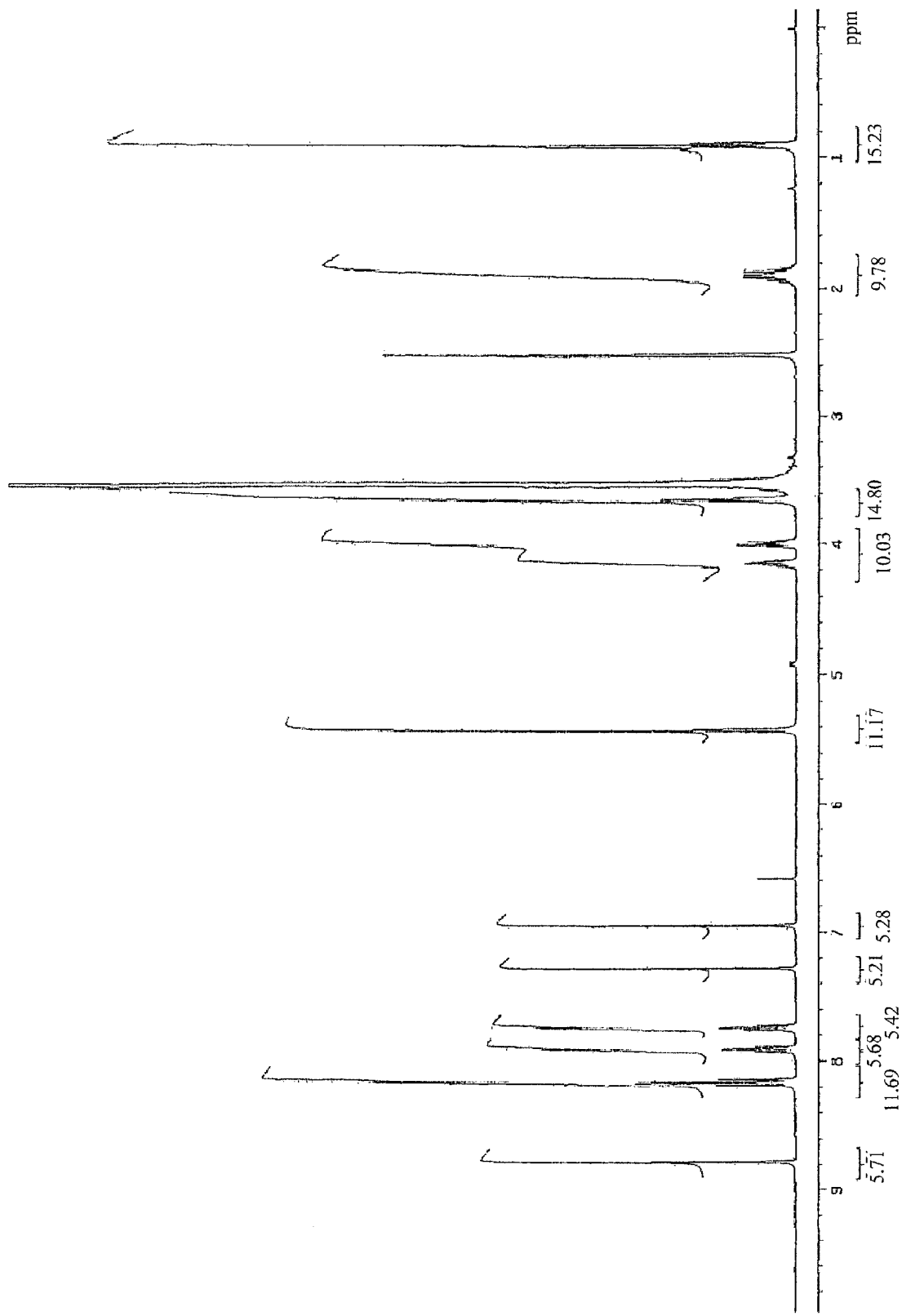
FIG. 7 shows a D$_2$O exchange spectrum of 5(S)-(2'-hydroxyethoxy)-20(S)-camptothecin in DMSO-d6.
Figure 8:
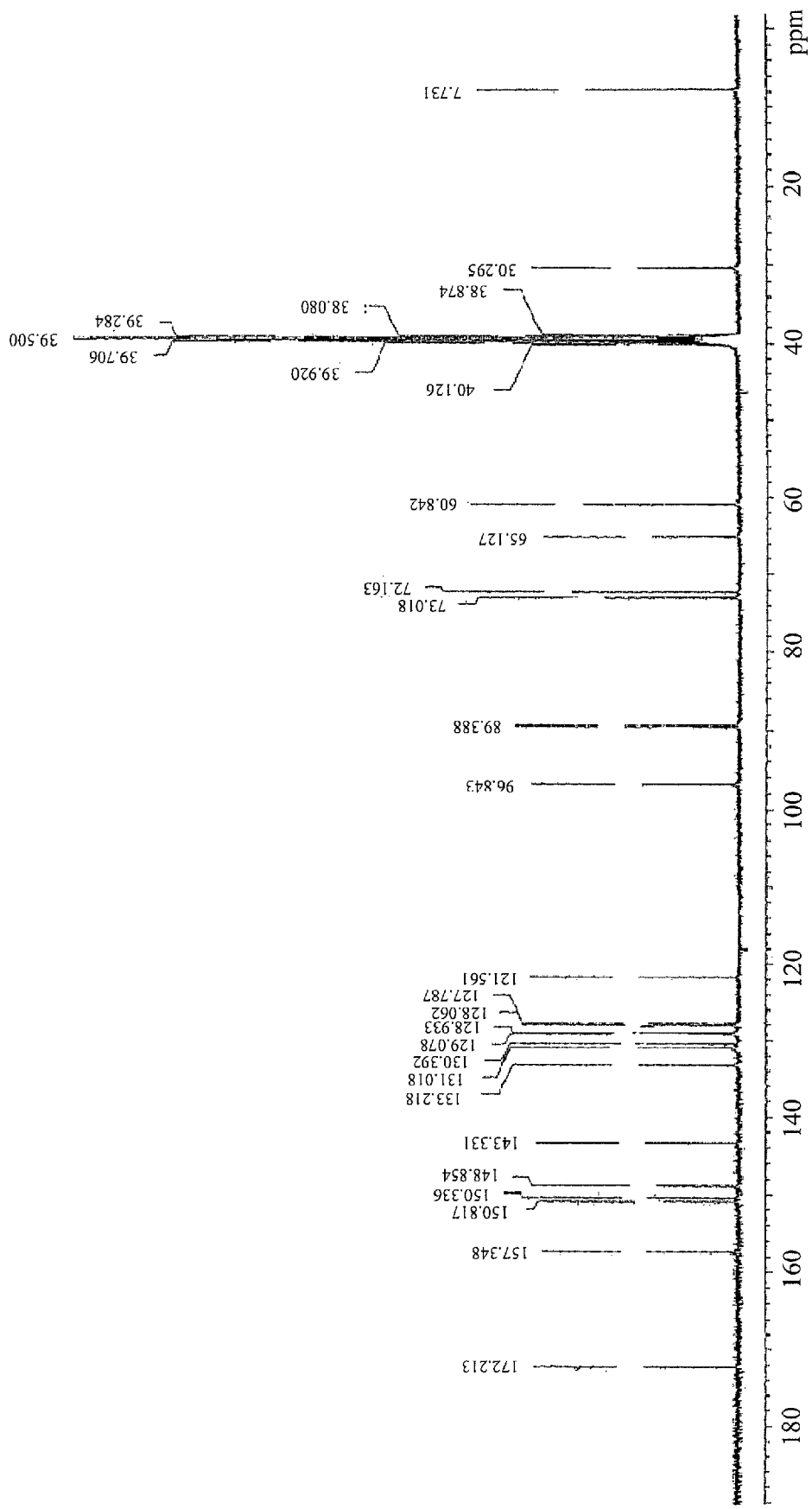
FIG. 8 shows a Carbon-13 nuclear magnetic resonance ($^{13}$C NMR) spectrum of 5(S)-(2'-hydroxyethoxy)-20(S)-camptothecin in DMSO-d6.

Nuclear Magnetic Resonance (NMR) Study:

The $^1$H and $^{13}$C NMR testing of 5(S)-CPT in DMSO-d$_6$ was done at 400 MHz on a Variane Mercury Plus Fourier Transform (FT) NMR spectrometer. $^1$H and $^{13}$C NMR chemical shifts are reported on the δ scale in ppm, relative to TMS (δ0.00) and DMSO-d$_6$ (δ39.50) as internal standards respectively. The $^1$H and $^{13}$C NMR spectra for 5(S)-CPT are shown in FIG. 6 and FIG. 8, respectively. The signals at δ4.82 and 6.55 ppm were found to be due to exchangeable protons from D$_2$O exchange spectrum (See FIG. 7).

Figure 9:
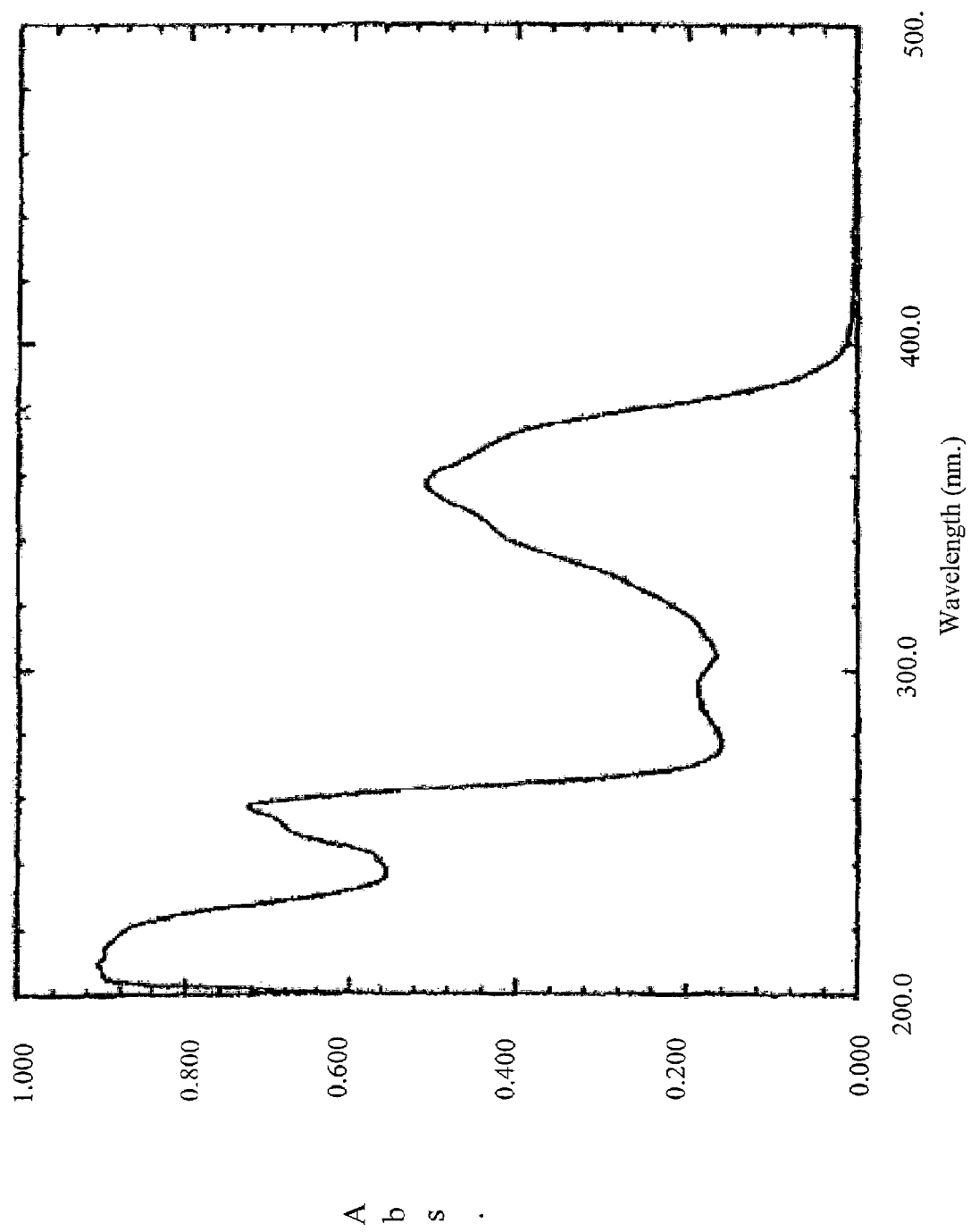
FIG. 9 shows an ultra violet (UV) spectrum of a solid form embodiment of 5(S)-(2'-hydroxyethoxy)-20(S)-camptothecin.

Ultraviolet Spectrophotometry (UV Spectrum):

The UV spectrum of 5(S)-CPT was recorded in methanol (concentration=0.001% w/v) on a Shimadzu 2100 UV-Visible Spectrophotomer. The resulting spectra is shown in FIG. 9, and exhibits a four peak maxima at λ 357, 293, 257 and 207 nm.

Crystalline Forms of 5(S)-CPT:

In one embodiment, 5(S)-CPT is isolated in crystalline form, which exists substantially free from water (i.e., essentially anhydrous). The term "substantially free from water" means the presence of less than about 1.0% water w/w and even specifically less than about 0.5% water w/w as measured by Karl Fisher analysis or TGA. In this Form, 5(S)-CPT has the advantageous property that no appreciable change in water content was observed during accelerated stability testing under conditions of 40° C.±2° C./75% RH±5% RH for 6 months as measured by Karl Fisher analysis and was found to be non-hygroscopic. The product is stable for 6 months under accelerated stability testing conditions of 40° C.±2° C./75% RH±5% RH and stable for 24 months under long term stability testing conditions at 30° C.±2° C./65%±5% RH.

Another embodiment of the present invention provides crystalline 5(S)-CPT having a Diffrential Scanning Calorimetry thermogram, an X-ray powder diffraction pattern, an X-ray crystal structure, a Fourier Transform Infra Red spectrum, a Proton Nuclear Magnetic Resonance spectrum, a D$_2$O exchange spectrum, a Carbon-13 Nuclear Magnetic Resonance spectrum, a UV spectrum as shown in FIG. 1, FIG. 2, FIG. 3, FIG. 5, FIG. 6, FIG. 7, FIG. 8 and FIG. 9, respectively.

Figure 5:
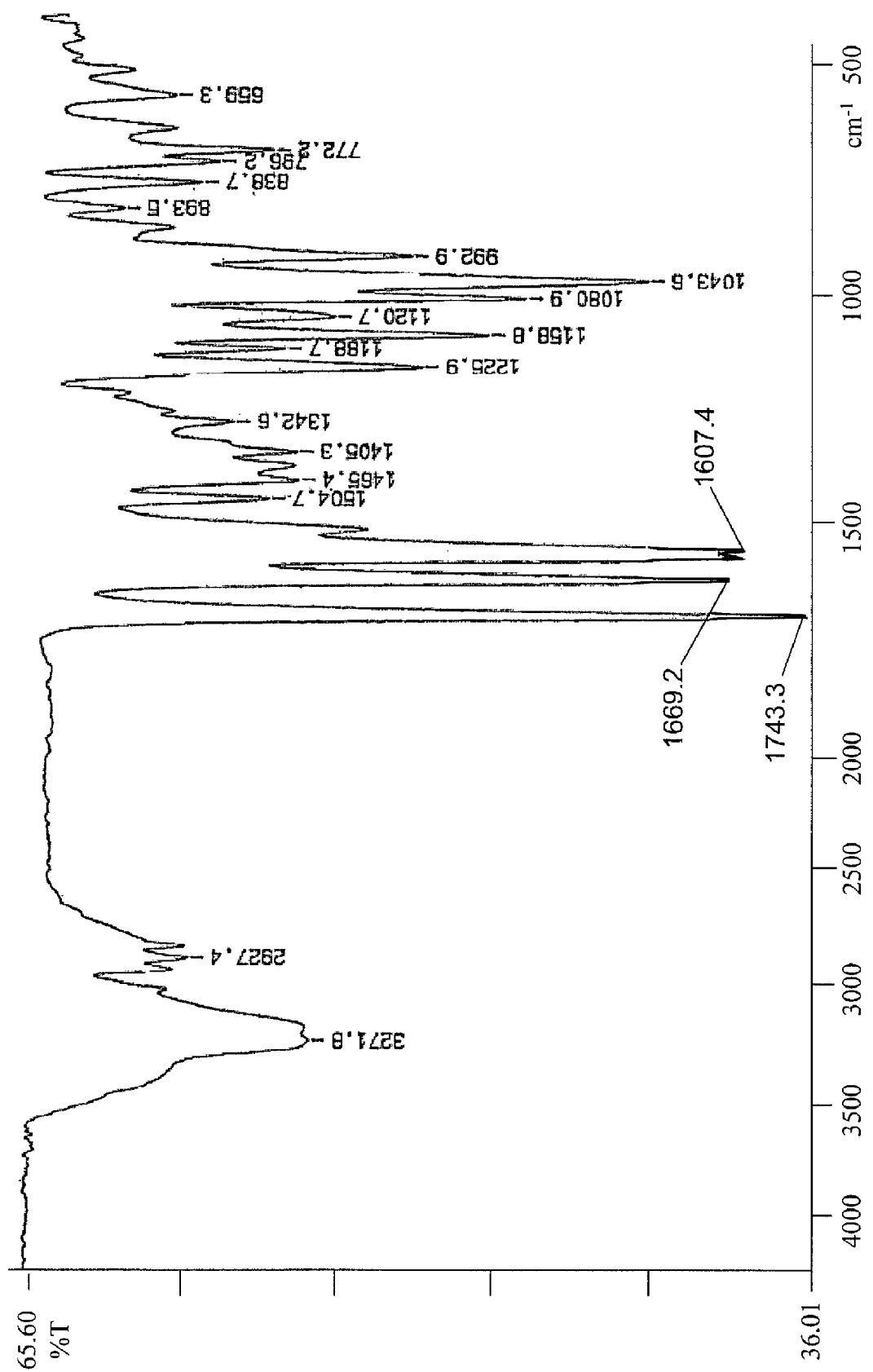
FIG. 5 shows a Fourier Transform Infra Red (FT-IR) spectrum of an embodiment of a solid form 5(S)-(2'-hydroxyethoxy)-20(S)-camptothecin of the present invention.

One aspect of the present invention provides crystalline 5(S)-CPT having a Diffrential Scanning Calorimetry thermogram, an X-ray powder diffraction pattern and a Fourier Transform Infra Red spectrum as shown in FIG. 1, FIG. 2 and FIG. 5, respectively.

Another aspect of the present invention provides crystalline 5(S)-CPT having a Differential Scanning Calorimetry thermogram and an X-ray powder diffraction pattern as shown in FIG. 1 and FIG. 2, respectively.

Another embodiment of the present invention provides crystalline 5(S)-CPT having an X-ray powder diffraction pattern as shown in FIG. 2.

Another embodiment of the present invention provides an anhydrous crystalline form of 5(S)-CPT having an XRPD pattern that comprises at least one diffraction peak selected from the group consisting of 7.2±0.1, 9.4±0.1, 11.02±0.1, 12.00±0.1, 14.54±0.1, 15.20±0.1, and 18.92±0.1 degrees 2θ. In one embodiment, this crystalline form has an XRPD pattern that comprises a diffraction peak at 7.2±0.1 degrees 2θ. In another embodiment, this crystalline form has a XRPD pattern that comprises a diffraction peak at 7.2±0.1 degrees 2θ, and further comprises at least one additional diffraction peak selected from the group consisting of 9.4±0.1, 11.02±0.1, 12.00±0.1, 14.54±0.1, 15.20±0.1, and 18.92±0.1 degrees 2θ.

Another embodiment of the present invention provides crystalline 5(S)-CPT having an FT-IR spectrum that comprises at least one absorption band selected from the group consisting of 3271±2, 1743±2, 1669±2, 1607±2, 1225±2, 1158±2, 1043±2 and 992±2 cm$^{-1}$. In one embodiment, this crystalline form has an FT-IR spectrum that comprises an absorption band at 1743±2 cm$^{-1}$. In another embodiment, this crystalline form has an FT-IR spectrum that comprises an absorption band at 1743±2 cm$^{-1}$, and further comprises at least one absorption band selected from the group consisting of 3271±2, 1669±2, 1607±2, 1225±2, 1158±2, 1043±2 and 992±2 cm$^{-1}$.

In one suitable embodiment, the crystalline 5(S)-CPT has an XRPD pattern comprising a diffraction peak at 7.2±0.1 degrees 2θ, and an FT-IR spectrum comprising an absorption band at 1743±2 cm$^{-1}$.

In another embodiment, crystalline 5(S)-CPT has an XRPD pattern comprising a diffraction peak at 7.2±0.1 degrees 2θ, and an FT-IR spectrum comprising absorption bands at 3271±2 and 1743±2 cm$^{-1}$.

In another embodiment, the present crystalline 5(S)-CPT has an XRPD pattern comprising diffraction peaks at 7.2±0.1 and 9.4±0.1 degrees 2θ and an FT-IR spectrum comprising an absorption band at 1743±2 cm$^{-1}$.

In another embodiment, the crystalline 5(S)-CPT has an XRPD pattern comprising diffraction peaks at 7.2±0.1 and 9.4±0.1 degrees 2θ, and an FT-IR spectrum comprising absorption bands at 3271±2 and 1743±2 cm$^{-1}$.

In another embodiment, the crystalline 5(S)-CPT has an XRPD pattern comprising diffraction peaks at 7.2±0.1, 9.4±0.1, 11.02±0.1, 12.00±0.1, 14.54±0.1, 15.20±0.1, and 18.92±0.1 degrees 2θ, and an FT-IR spectrum comprising absorption bands at 3271±2, 1743±2, 1669±2, 1607±2, 1225±2, 1158±2, 1043±2 and 992±2 cm$^{-1}$.

In another embodiment, the crystalline 5(S)-CPT has an XRPD pattern comprising diffraction peaks at 7.2±0.1, 9.4±0.1, 11.02±0.1, 12.00±0.1, 14.54±0.1, 15.20±0.1, and 18.92±0.1 degrees 2θ, and a melting point in a range of about 234° C. to about 238° C.

Figure 12:
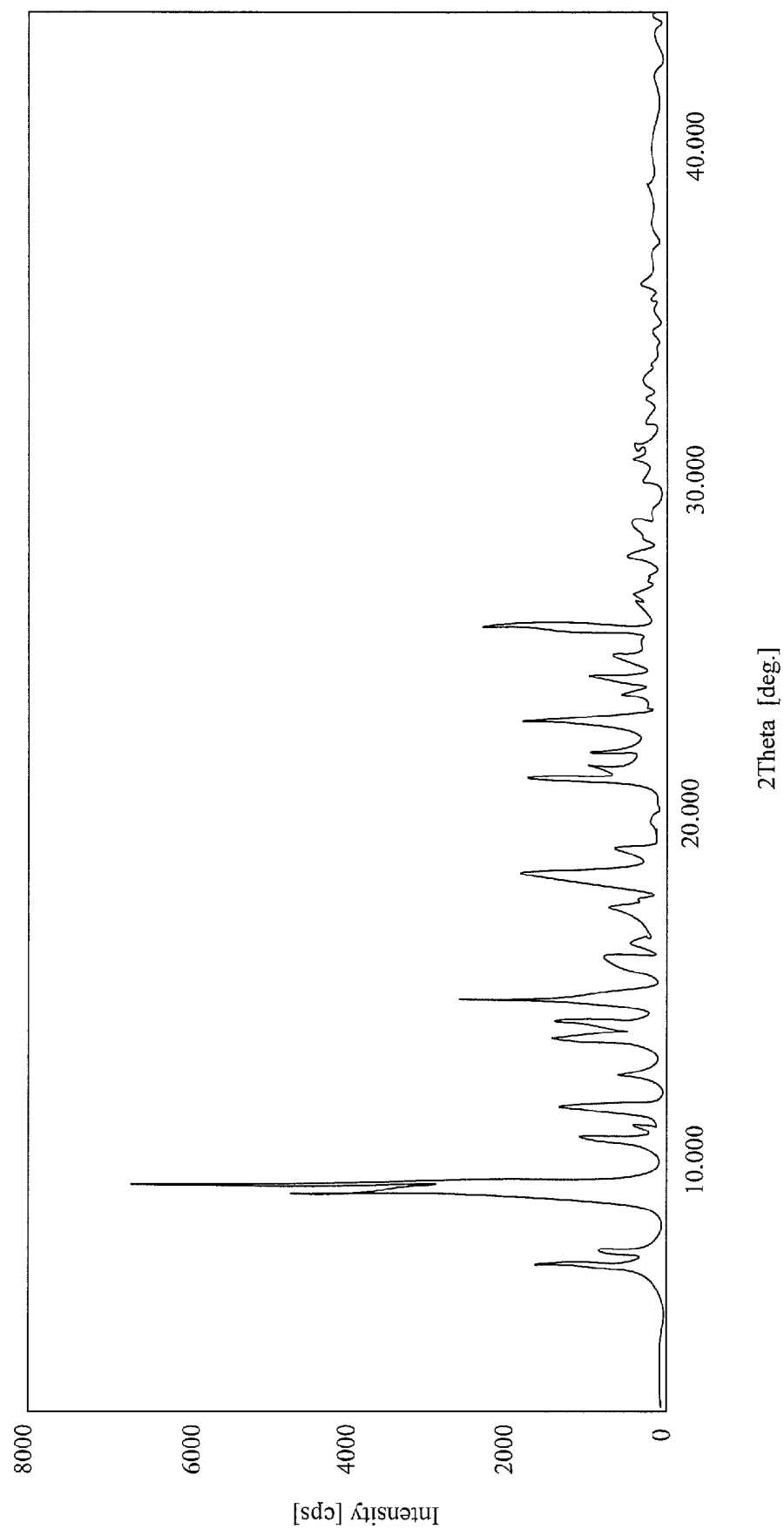
FIG. 12 shows an X-ray powder diffraction pattern of 5(RS)-(2'-hydroxyethoxy)-20(S)-camptothecin.
Figure 13:
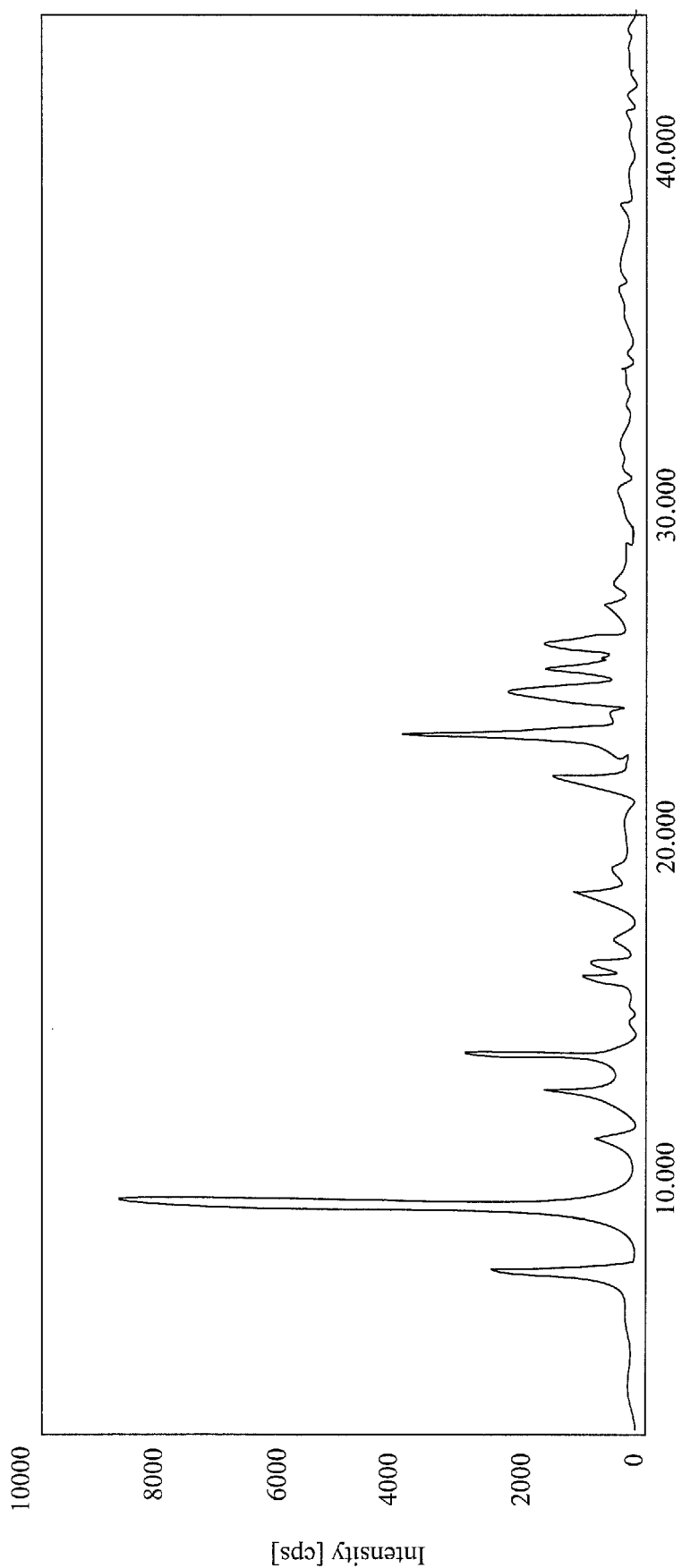
FIG. 13 shows a X-ray powder diffraction pattern of 5(R)-(2'-hydroxyethoxy)-20(S)-camptothecin.

For comparison purposes, the X-ray powder diffraction patterns for 5(RS)-(2'-hydroxyethoxy)-20(S)-camptothecin, produced according to U.S. Pat. No. 6,177,439, and 5(R)-CPT are shown in FIG. 12 and FIG. 13, respectively.

Figure 10:
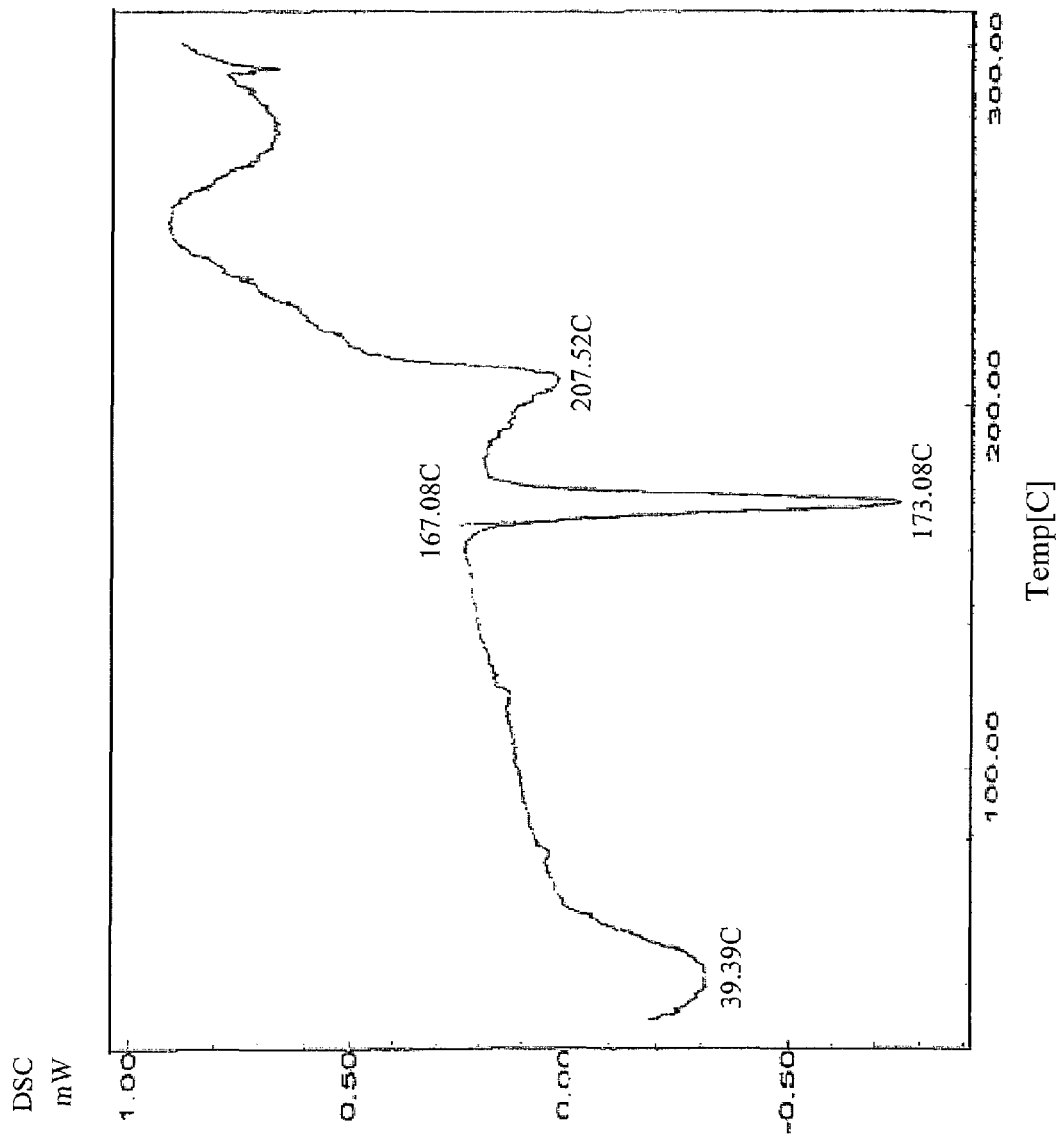
FIG. 10 shows the DSC thermogram of 5(RS)-(2'-hydroxyethoxy)-20(S)-camptothecin.
Figure 11:
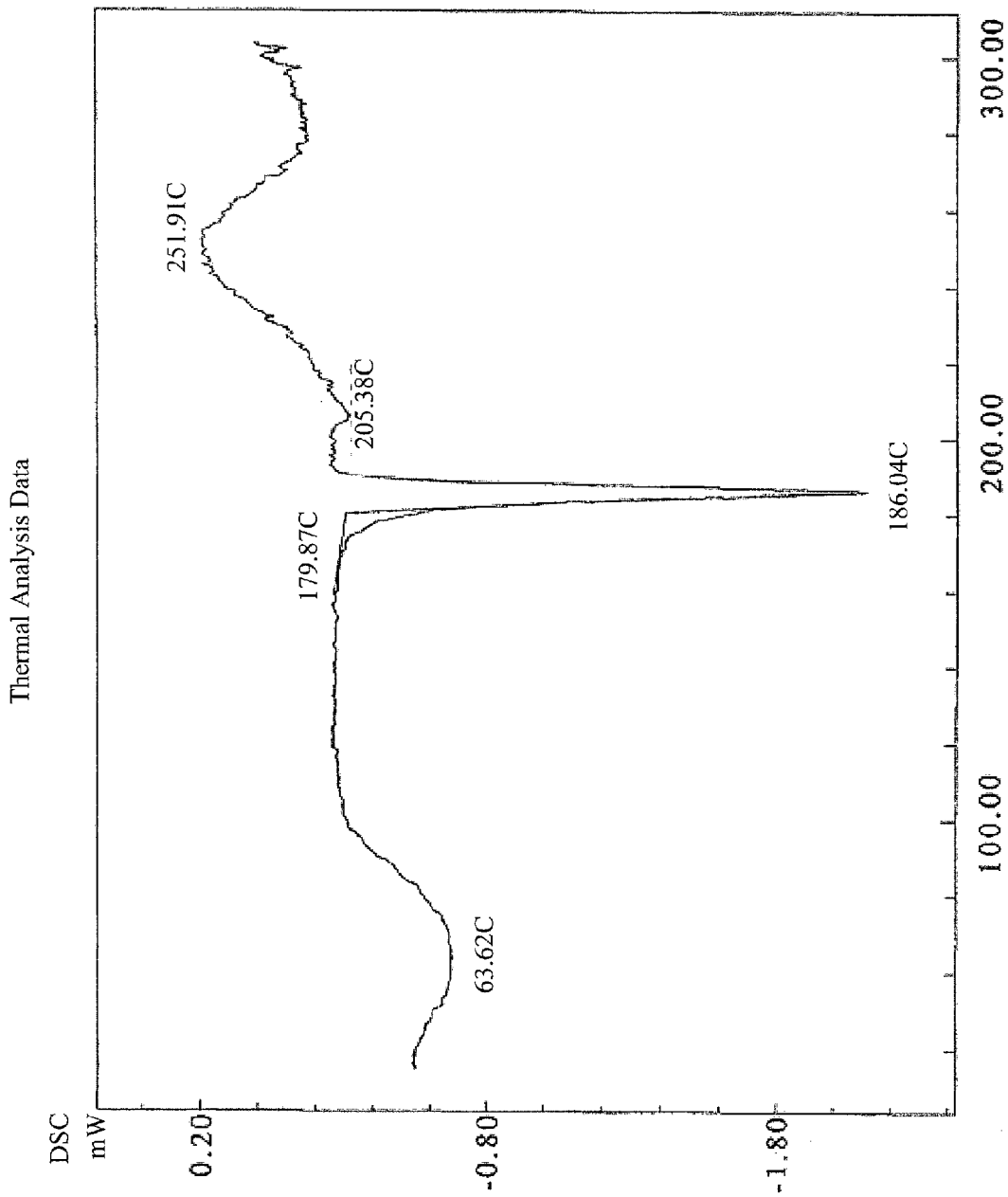
FIG. 11 shows a DSC thermogram of a solid form of 5(R)-(2'-hydroxyethoxy)-20(S)-camptothecin.

Another embodiment of the present invention provides crystalline 5(S)-CPT that is substantially free of 5(R)-CPT. This material is also characterized by a single melting endotherm peak at about 236° C. as measured by DSC and shown in FIG. 1. In contrast, the DSC profile for the diastereoisomer 5-(2'-hydroxyethoxy)-20(S)-camptothecin as produced according to U.S. Pat. No. 6,177,439 and shown in FIG. 10 is much more complex, and shows an endotherm peak at about 39° C., a second endotherm peak at about 173° C. and a third endotherm peak at about 207° C., consistent with the 190° C. melting point listed in U.S. Pat. No. 6,177,439 for this compound. Furthermore, a DSC profile for 5(R)-CPT, as shown in FIG. 11, shows an endotherm peak at about 63° C., a second endotherm peak at about 186° C. and a third endotherm peak at about 205° C. This again confirms the different solid state structures of 5(S)-CPT and 5(R)-CPT.

Further, the higher melting point of crystalline 5(S)-CPT indicates a greater stability of that form as compared with 5(R)-CPT.

Another embodiment of the present invention provides crystalline 5(S)-CPT, having an NMR pattern as represented by the values given in Table 2.

TABLE 2

$^1$H and $^{13}$C NMR assignment for 5(S)-CPT.

| Position* | $^1$H | δ(PPM) | J (Hz)# | $^{13}$C |
|---|---|---|---|---|
| 2 | — | — | — | 150.82 |
| 3 | — | — | — | 143.33 |
| 5 | 1H | 6.95 | — | 89.39 |
| 6 | — | — | — | 130.39 |
| 7 | 1H | 8.78 | — | 133.22 |
| 8 | — | — | — | 127.79 |
| 9 | 1H | 8.16 | — | 128.93 |
| 10 | 1H | 7.73 | t(7.6) | 128.06 |
| 11 | 1H | 7.88 | t(7.6) | 131.02 |
| 12 | 1H | 8.16 | — | 129.08 |
| 13 | — | — | — | 148.85 |
| 14 | 1H | 7.26 | S | 96.84 |
| 15 | — | — | — | 150.34 |
| 16 | — | — | — | 121.56 |
| 16a | — | — | — | 157.35 |
| 17 | 2H | 5.42 | dd(16.4, 2.4) | 65.13 |
| 18 | 3H | 0.90 | t(7.6) | 7.73 |
| 19 | 2H | 1.89 | M | 30.29 |
| 20 | — | — | — | 72.16 |
| 21 | — | — | — | 172.21 |
| 22 | Ha | 4.17 | m | 73.02 |
|  | Hb | 4.00 | m |  |
| 23 | 2H | 3.65 | M | 60.84 |
| 24 | OH | 4.82 | t(5.2) | — |
| 25 | OH | 6.55 | S | — |

*Refer the structural formula given above the numbering.
This column gives the multiplicity and coupling constant.
s—singlet, t—triplet, dd—doublet of doublet, m—multiplet.

Crystalline 5(S)-CPT that is substantially free of 5(R)-CPT may be obtained by the processes that are described below, which form a further aspect of the present invention.

A further aspect of the present invention provides a process for the preparation of an anhydrous crystalline form of 5(S)-CPT. In this method, 5(RS)-(2'-hydroxyethoxy)-20(S)-camptothecin, obtained by the process disclosed in U.S. Pat. No. 6,177,439, or a similar process, is suspended in a suitable organic solvent, such as n-butanol (n-BuOH), tetrahydrofuran (THF), ethyl acetate (EtOAc), isopropyl alcohol (IPA), actone, methyl isobutyl ketone (MIBK), ethyl methyl ketone (EMK), acetonitrile (ACN), n-butyl acetate, methanol (MeOH), ethanol (EtOH), n-propanol (n-PrOH), isopropanol (i-PrOH), amyl alcohol, and the like, or mixtures thereof, and refluxed over a period of about 2-6 hours. The suspension is slowly cooled to about 40-45° C. such that a complete precipitate is formed. The precipitate is isolated using conventional techniques, such as filtration, and can be washed with the same or other suitable organic solvent and dried under vacuum to yield solid 5(S)-CPT that is substantially free from 5(R)-CPT. The product can be further enriched by repeatedly refluxing from about 2-4 times in the same or other suitable organic solvent.

In another embodiment of the present invention, there is provided crystalline 5(S)-CPT containing less than about 1.5% of the camptothecin dimer shown in formula V, or less than about 1% of the camptothecin dimer of formula V, or less than about 0.8% of the camptothecin dimer, or even less than about 0.5% of the camptothecin dimer, or yet even less than about 0.1% of the camptothecin dimer, all on a w/w basis.

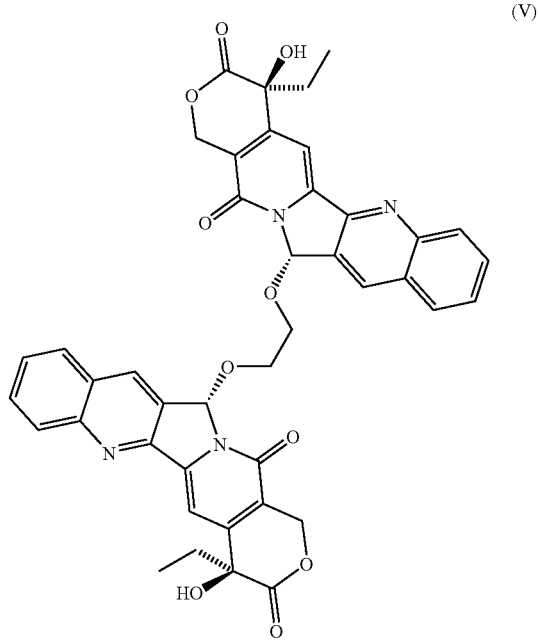

(V)

The crystalline form of 5(S)-CPT differs from the diastereomeric mixture 5(RS)-(2'-hydroxyethoxy)-20(S)-camptothecin in several important characteristics, including, for example, toxicity, in vivo anti-tumor activity, bioavailability and topoisomerase I inhibition. Furthermore, it has now been also discovered that crystalline 5(S)-CPT which is substantially free from 5(R)-CPT is a desirable anti-cancer pharmaceutical compound.

In the present invention, the crystalline form of 5(S)-CPT is administered to a subject according to standard routes of drug delivery that are well known to one of ordinary skill in the art for the purpose of treating cancer.

The crystalline 5(S)-CPT can be supplied as a pure compound, or in the form of a pharmaceutically active salt. Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, b-hydroxybutyric, galactaric and galacturonic acids.

Suitable pharmaceutically-acceptable base addition salts of compounds of the present invention include metallic ion salts and organic ion salts. More preferred metallic ion salts include, but are not limited to appropriate alkali metal (group Ia) salts, alkaline earth metal (group IIa) salts and other physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound of the present invention.

The present crystalline 5(S)-CPT can be provided in a pharmaceutically acceptable carrier and excipient (wherein all "carriers" and "excipients" can be described by either term) to form a pharmaceutical composition. Pharmaceutically acceptable carriers and excipients include, but are not limited to, physiological saline, Ringer's solution, phosphate solution or buffer, buffered saline and other carriers known in the art. Pharmaceutical compositions may also include stabilizers, anti-oxidants, colorants, and diluents. Pharmaceutically acceptable carriers and additives are chosen such that side effects from the pharmaceutical compound are minimized and the performance of the compound is not canceled or inhibited to such an extent that treatment is ineffective.

In an embodiment of the present invention, the pharmaceutical composition containing 5(S)-CPT is optionally substantially free of 5(R)-CPT.

The pharmaceutical composition typically contains from 0.1 to 50% w/w, or from 1 to 20% w/w, of active crystalline 5(S)-CPT compound, the remainder of the composition being the pharmaceutically acceptable carrier or carriers, diluents or solvents. Preferably, the pharmaceutical composition is in a unit dosage form containing appropriate quantities of the active compound, e.g., an amount effective to achieve the desired purpose.

The present pharmaceutical compositions may be administered enterally and/or parenterally. Oral (intra-gastric) is a preferred route of administration. Pharmaceutically acceptable carriers can be in solid dosage forms for the methods of the present invention, which include tablets, capsules, pills, and granules, which can be prepared with coatings and shells, such as enteric coatings and others well known in the art. Liquid dosage forms for oral administration include pharmaceutically acceptable emulsions, solutions, suspensions, syrups, and elixirs.

Parenteral administration includes subcutaneous, intramuscular, intradermal, intramammary, intravenous, and other administrative methods known in the art. Enteral administration includes solution, tablets, sustained release capsules, enteric coated capsules, and syrups. When administered, the pharmaceutical composition may be at or near body temperature.

Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be, for example, inert diluents, such as calcium carbonate, sodium carbonate, lactose, calcium phosphate or sodium phosphate, granulating and disintegrating agents, for example, maize starch, or alginic acid, binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the crystalline 5(S)-CPT is mixed with an inert solid diluent, for example, calcium carbonate, calcium phosphate or kaolin, or as soft gelatin capsules wherein the active ingredients are present as such, or mixed with water or an oil medium, for example, peanut oil, liquid paraffin, or olive oil.

Aqueous suspensions can be produced that contain the crystalline 5(S)-CPT in a mixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate.

The aqueous suspensions may also contain one or more preservatives, for example, ethyl or n-propyl p-hydroxybenzoate, one or more coloring agents, one or more flavoring agents, or one or more sweetening agents, such as sucrose or saccharin.

Oily suspensions may be formulated by suspending the crystalline 5(S)-CPT in an omega-3 fatty acid, a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol.

Dispersible powders and granules suitable for preparation of an aqueous suspension by the addition of water provide the crystalline 5(S)-CPT in admixture with a dispersing or wetting agent, a suspending agent and one or more preservatives. Suitable dispersing or wetting agents and suspending agents are exemplified by those already mentioned above. Additional excipients, for example sweetening, flavoring and coloring agents, may also be present.

The crystalline 5(S)-CPT and compositions comprising the same can also be administered parenterally, either subcutaneously, or intravenously, or intramuscularly, or intrasternally, or by infusion techniques, in the form of sterile injectable aqueous or oleaginous suspensions. Such suspensions may be formulated according to the known art using those suitable dispersing of wetting agents and suspending agents which have been mentioned above or other acceptable agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed, including synthetic mono- or diglycerides. In addition, n-3 polyunsaturated fatty acids may find use in the preparation of injectables.

Administration can also be by inhalation, in the form of aerosols or solutions for nebulizers, or rectally, in the form of suppositories prepared by mixing the drug with a suitable non-irritating excipient which is solid at ordinary temperature, but liquid at the rectal temperature and will therefore, melt in the rectum to release the drug. Such materials are cocoa butter and polyethylene glycols.

Also encompassed by the present invention is buccal or "sub-lingual" administration, which includes lozenges or a chewable gum comprising the compounds, set forth herein. The compounds can be deposited in a flavored base, usually sucrose, and acacia or tragacanth, and pastilles comprising the compounds in an inert base such as gelatin and glycerin or sucrose and acacia.

Topical delivery systems are also encompassed by the present invention and include ointments, powders, sprays, creams, jellies, collyriums, solutions or suspensions.

Powders have the advantage of sticking to moist surfaces, and consequently, can remain active for longer periods. Therefore, powders are especially attractive for treating cancers in, for example the otic canal. For much the same reason, creams are also effective pharmaceutically acceptable carriers.

The compositions of the present invention can optionally be supplemented with additional agents such as, for example, viscosity enhancers, preservatives, surfactants and penetration enhancers.

Such viscosity-building agents include, for example, polyvinyl alcohol, polyvinyl pyrrolidone, methylcellulose, hydroxy propyl methylcellulose, hydroxyethyl cellulose, carboxymethyl cellulose, hydroxy propyl cellulose or other agents know to those skilled in the art. Such agents are typically employed at a level of from 0.01% to 2% by weight.

Preservatives are optionally employed to prevent microbial contamination during use. Suitable preservatives include: polyquaternium-1, benzalkonium chloride, thimerosal, chlorobutanol, methyl paraben, propyl paraben, phenylethyl alcohol, edetate disodium, sorbic acid, or other agents known to those skilled in the art. The use of polyquaternium-1 as the antimicrobial preservative is preferred. Typically, such preservatives are employed at a level of from 0.001% to 1.0% by weight.

The solubility of the components of the present compositions may be enhanced by a surfactant or other appropriate co-solvent in the composition. Such co-solvents include polysorbate 20, 60, and 80, polyoxyethylene/polyoxypropylene surfactants (e.g. Pluronic F-68, F-84 and P-103), cyclodextrin, or other agents known to those skilled in the art. Typically, such co-solvents are employed at a level of from 0.01% to 2% by weight.

Pharmaceutically acceptable excipients and carriers encompass all the foregoing and the like. The above considerations concerning effective formulations and administration procedures are well known in the art and are described in standard textbooks. See e.g. Gennaro, A. R., Remington: The Science and Practice of Pharmacy, 20th Edition, (Lippincott, Williams and Wilkins), 2000; Hoover, John E., Remington's Pharmaceutical Sciences, Mack Publishing Co., Easton Pa., 1975; Liberman, et al., Eds., Pharmaceutical Dosage Forms, Marcel Decker, New York, N.Y., 1980; and Kibbe, et al., Eds., Handbook of Pharmaceutical Excipients (3rd Ed.), American Pharmaceutical Association, Washington, 1999.

For purposes of the present invention, it is preferred that the amount of a crystalline 5(S)-CPT comprises an effective amount of the compound. Thus, the present invention encompasses a method of preventing or treating cancer, neoplasia, and/or a neoplasia-related disease or disorder (which together will be referred to herein as "cancer"), where such treatment can be administered to a subject in need of such prevention or treatment, the method comprising administering an effective amount of the crystalline 5(S)-CPT as described herein to a subject.

In determining the effective amount or dose of crystalline 5(S)-CPT, a number of factors are considered by the attending diagnostician, including, but not limited to, the potency and duration of action of the compounds used, the nature and severity of the illness to be treated, as well as the sex, age, weight, general health and individual responsiveness of the patient to be treated, and other relevant circumstances. It will be appreciated that the amount of the crystalline 5(S)-CPT required for use in the treatment or prevention of cancer will vary within wide limits and will be adjusted to the individual requirements in each particular case.

For any compound, the therapeutically effective dose can be estimated initially either in cell culture or in animal models. The therapeutically effective dose refers to the amount of active compound that ameliorates the condition or its symptoms. Therapeutic efficacy and toxicity in cell cultures or animal models may be determined by standard pharmaceutical procedures (e.g., $ED_{50}$: the dose therapeutically effective in 50% of the population; $LD_{50}$: the dose lethal to 50% of the population). The data obtained from cell culture and animal models can then be used to formulate a range of dosage for the compound for use in patients.

In general, for administration to adults, an appropriate daily dosage is described herein, although the limits that are identified as being preferred may be exceeded if expedient. The daily dosage can be administered as a single dosage or in divided dosages. Those skilled in the art will appreciate that dosages may also be determined with guidance from Goodman & Goldman's *The Pharmacological Basis of Therapeutics, Ninth Edition* (1996), Appendix II, pp. 1707-1711. A typical recommended daily dosage regimen will generally range from about 0.01 mg/kg/day to about 50 mg/kg/day, or from about 0.05 mg/kg/day to about 25 mg/kg/day, or from about 0.1 mg/kg/day to about 10 mg/kg/day, or from about 0.1 mg/kg/day to about 5 mg/kg/day, or even from about 0.2 mg/kg/day to about 3 mg/kg/day.

In one embodiment, the crystalline 5(S)-CPT can be provided as hard gelatin capsules for oral administration containing from about 1 mg to about 1000 mg of 5(S)-CPT per capsule, or from about 2 mg to about 500 mg, or from about 5 mg to about 250 mg of 5(S)-CPT per capsule. When the subject to which the 5(S)-CPT is administered is an adult human, the daily dosage of the 5(S)-CPT can be from about 0.01 mg/kg/day to about 50 mg/kg/day, or from about 0.05 mg/kg/day to about 25 mg/kg/day, or from about 0.1 mg/kg/day to about 10 mg/kg/day, or from about 0.1 mg/kg/day to about 5 mg/kg/day, or even from about 0.2 mg/kg/day to about 3 mg/kg/day.

As used herein, the term "subject" for purposes of treatment includes any subject, and can be a subject who is in need of the treatment of cancer. As used herein, the terms "subject in need of" refer to any subject who is suffering from or is predisposed to cancer. The terms "subject in need of" also refer to any subject that requires a lower dose of conventional cancer treatment agents. In addition, the terms "subject in need of" means any subject who requires a reduction in the side-effects of a conventional treatment agent. Furthermore, the terms "subject in need of" means any subject who requires improved tolerability to any conventional treatment agent for cancer therapy.

The subject is typically an animal, and yet more typically is a mammal. "Mammal", as that term is used herein, refers to any animal classified as a mammal, including humans, domestic and farm animals, zoo, sports, or pet animals, such as dogs, horses, cats, cattle, etc. The subject may also be a human subject who is at risk for developing cancer or at risk for a relapse of cancer.

The methods and compositions of the present invention may be used for the treatment or prevention of several cancers including, but not limited to, ovarian cancer, osteosarcoma, leukemia, lymphoma, small cell lung cancer, non-small cell lung cancer, central nervous system (CNS) cancer, breast cancer, colorectal cancer, renal cancer, bladder cancer, breast cancer, epidermoid cancer, lung cancer, melanoma, prostate cancer, uterine cancer, soft tissue sarcoma, pancreatic cancer and rhabdomyosarcoma.

The compounds and preparations of the present invention can also be used for the treatment of colon cancer, ovarian cancer and osteosarcoma.

The compounds and preparations of the present invention can also be used for the treatment of osteosarcoma, colorectal cancer and pancreatic cancer.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples all percentages are given on a weight basis unless otherwise indicated.

EXAMPLE 1

This example illustrates the preparation of 5(S)-(2'-hydroxyethoxy)-20(S)-camptothecin.

5(RS)-(2'-hydroxyethoxy)-20(S)-camptothecin (75 grams) prepared as described in Example-26 of U.S. Pat. No. 6,177,439, was suspended in n-butanol (about 600 ml) and refluxed over a period of about 2-3 hours. The reaction mass temperature was reduced over a period of 1-4 hours to about 40-50° C., and the solid material obtained was filtered, washed with n-butanol (about 15-20 ml) and dried under vacuum at about 50-55° C. to yield solid 5(S)-(2'-hydroxyethoxy)-20(S)-camptothecin substantially free of 5(R)-(2'-hydroxyethoxy)-20(S)-camptothecin. The product was further enriched by repeatedly refluxing in n-butanol (generally 2-4 times; yield 25-35 grams). The final dried product was characterized by X-ray powder diffraction and provided the XRPD pattern shown in FIG. 2, with peaks at about 4.68, 7.22, 9.4, 11.02, 12.00, 14.14, 14.54, 15.20, 16.22, 17.10, 17.32, 17.94, 18.92, 19.16, 19.70, 21.86, 22.22, 22.74, 23.28, 23.72, 24.22, 24.4, 25.36, 26.42, 27.12, 27.66, 28.58, 29.12, 29.46, 30.62, 30.78, 31.42, 31.94, 32.46, 32.78, 33.30, 33.54, 33.98, 35.18, 36.74, 37.62, 38.28, 38.92, 39.82, 40.38, 42.08, 42.22 and 43.98 degrees 2θ.

EXAMPLE 2

This example illustrates an optional method for the preparation of 5(S)-(2'-hydroxyethoxy)-20(S)-camptothecin.

A sample of 5(RS)-(2'-hydroxyethoxy)-20(S)-camptothecin (75 grams) prepared as described in Example-26 of U.S. Pat. No. 6,177,439, was suspended in tetrahydrofuran (THF) (1125 ml) and refluxed over a period of 2-3 hours. The reaction mass temperature was lowered to 40-45° C. over a period of about 1-4 hours, and the resulting solids were filtered, washed with THF (15-20 ml) and dried under vacuum at 50-55° C. to yield solid 5(S)-(2'-hydroxyethoxy)-20(S)-camptothecin. The product was further enriched by repeatedly refluxing in THF (generally 2-4 times; yield 15-20 grams). The final dried product was characterized by the X-ray powder diffraction pattern shown in FIG. 2.

EXAMPLE 3

This example shows the unexpectedly high topoisomerase I inhibition activity of 5(S)-CPT as compared against the 5(RS)-CPT diastereoisomer and against the 5(R)-CPT diastereoisomer.

Preparation of 5(S)-CPT, 5(R)-CPT and 5(RS)-CPT:

A sample of 5(RS)-(2'-hydroxyethoxy)-20(S)-camptothecin (75 grams) prepared as described in Example-26 of U.S. Pat. No. 6,177,439, was suspended in n-butanol (about 600 ml) and refluxed over a period of about 2-3 hours. The reaction mass temperature was reduced over a period of 1-4 hours to about 40-50° C., and the solid material obtained was filtered, washed with n-butanol (about 15-20 ml) and dried under vacuum at about 50-55° C. to yield solid 5(S)-(2'-hydroxyethoxy)-20(S)-camptothecin substantially free of 5(R)-(2'-hydroxyethoxy)-20(S)-camptothecin. The product was further enriched to yield 5(S)-CPT that was substantially free of 5(R)-CPT by repeatedly refluxing in n-butanol (generally 2-4 times; yield 25-35 grams).

5(R)-CPT was isolated from the mother liquor by dropwise addition of n-heptane followed by filtration using a 10μ Nutche filter.

5(RS)-(2'-hydroxyethoxy)-20(S)-camptothecin was obtained as described in Example 26 of U.S. Pat. No. 6,177,439.

Topoisomerase I Assay:

Topoisomerase I introduces transient nicks in DNA at specific sites. Detection of these transient DNA nicks requires trapping the enzyme on DNA in a nicked intermediate complex using protein denaturants. The resulting covalent DNA/ topo I complexes contain nicked open circular DNA which can be detected by agarose gel electrophoresis (with ethidium bromide). Trapping nicked intermediates is relatively inefficient, however, inhibitors, such as the natural product camptothecin, stabilize the intermediate and lead to an increase in the nicked DNA product. This forms the basis for a mechanistic drug screen designed to allow detection of agents that affect topoisomerase I by stabilizing the cleaved intermediate complex.

The TopoGEN® Topo I Drug Screening Kit (Topogen, Inc., Port Orange, Fla.) is designed to allow the investigator to quickly identify novel inhibitors of topoisomerase I. The kit allows the detection of novel compounds that either stabilize the nicked intermediate or otherwise inhibit catalytic activity of topoisomerase I.

Assay KIT used: Topogen ® Drug screening kit, Manufacturer: TOPOGEN, Cat No: 1018.
Each reaction mix contains:

| | |
|---|---|
| a. 10× Reaction buffer | 2 μl |
| b. TOPO I enzyme | 2 μl |
| c. pHOT I DNA | 1.2 μl (0.5 ug) |

-continued

| Assay KIT used: Topogen ® Drug screening kit, Manufacturer: TOPOGEN, Cat No: 1018. Each reaction mix contains: | |
|---|---|
| d. Water | 14.8 µl |
| Drug in DMSO | 1 µl |
| Total | 20 µl |

Protocol

The above reaction mixture is incubated at 37° C. for 30 minutes. The reaction is terminated by adding 2 µl of 10% SDS and the mixture is vortexed rapidly (SDS should be added while at 37° C. as cooling the tubes might reseal the nicked DNA). 10× Dye, about 2.5 µl per tube, is added and equal volumes of a mixture of chloroform and isoamyl alcohol (24:1) is added and centrifuged at 13000 rpm for 10 minutes. Samples are loaded on a 1% agarose gel and electrophoresed for 1 hour at 80 volts. The gel was viewed on UV transilluminator and the densitometric estimation of the bands was calculated.

Calculations:

The density of the DNA bands of both super coiled and relaxed forms of DNA was measured using the densitometer. The band intensity of treated (with single concentration of the test drug) and without the drug (i.e., the Control) were recorded. The percentage of relaxed form DNA compared to the supercoiled DNA was calculated for all the lanes including treated and control.

% inhibition of Topoisomerase activity was calculated as:

=(100−(100×(1/% inhibition in Control)×% inhibition in treated))

Table 3 shows the results of these tests and shows the in vitro topoisomerase I activities of 5(S)-CPT and 5(R)-CPT, which were substantially free of each other, compared with the activity of the 5(RS)-CPT.

TABLE 3

Topoisomerase I activity of 5(S)-CPT, 5(R)-CPT and 5(RS)-CPT.

| COMPOUND | $IC_{50}(\mu M)$ |
|---|---|
| 5(S)-CPT | 1.06 |
| 5(R)-CPT | 22 |
| 5(RS)-CPT | 12.5 |

The results show that the 5(S)-CPT is about 21-fold more active than 5(R)-CPT and about 12 times more active than 5(RS)-CPT in inhibiting topoisomerase I. Such differences in activity would not be expected based on structural differences between the diastereomers since it is known that, particularly in view of the importance of the E-ring in enzyme activity.

EXAMPLE 4

This example shows the anti-tumor activity of 5(S)-CPT against NC1-H460 (human small cell lung carcinoma) xenografts in nude mice as compared versus the activity of 5(RS)-CPT.

Samples of 5(S)-CPT and 5(RS)-CPT were provided as described in Example 3.

Protocol of Comparison Study of 5(RS)-CPT and 5(S)-CPT Against NCI-H460 Xenograft in Nude Mice:

To perform the NCI-H460 xenograft study, NCI-H460 tumor pieces measuring ~60 mm$^3$ were implanted in the space of dorsal lateral flanks of female athymic nude mice to initiate tumor growth. When the tumors were grown to ~150-1000 mm$^3$, animals were randomized into groups of five prior to initiating therapy. Each gram of 5(RS)-CPT was formulated to contain 102.65 mg active compound, 801.62 mg hydroxylpropyl beta cyclodextran, 80.62 mg dextrose anhydrous and 13.33 mg sodium carbonate. Each gram of 5(S)-CPT was formulated to contain 105.57 mg active compound, 800.99 mg hydroxylpropyl beta cyclodextran, 80.13 mg dextrose anhydrous and 13.34 mg sodium carbonate. Each gram of placebo was formulated to contain 895.2 mg hydroxylpropyl beta cyclodextran, 89.52 mg dextrose anhydrous and 14.9 mg sodium carbonate. Each formulation was dissolved in 2 ml sterile water and administered through oral route in a (d×5)$_2$ schedule. Tumor diameters were measured twice a week using a vernier caliper.

Tumor volumes were calculated assuming tumors to be ellipsoid using the formula:

$$V = (D \times d^2)/2,$$

where V (mm$^3$) is tumor volume, D is longest diameter in mm and d is shortest diameter in mm. Change in tumor volumes (Δ) for each treated (T) and control (C) group were calculated by subtracting the mean tumor volume on the first day of treatment (starting day) from the mean tumor volume on the specified observation day. These values were used to calculate a percentage growth (% T/C) using the formulas:

% $T/C = (\Delta T/\Delta C) \times 100$, where $\Delta T > 0$, or

% $T/C = (\Delta T/\Delta Ti) \times 100$, where $\Delta T < 0$ and

Ti is the mean tumor volume.

Percentage tumor growth inhibition (% TGI) was then calculated using the formula:

% $TGI = 100 - \% TC.$

All of the mice bearing subcutaneous tumors measuring approximately 150-800 mm$^3$ were treated with test compound through oral gavage using a (d×5)$_2$ schedule. Tumor diameters were measured twice in a week using vernier calipers and tumor volumes were calculated assuming tumors to be ellipsoid using the formula $V = (D \times d^2)/2$ where V (mm$^3$) is tumor volume, D is longest diameter in mm., and d is shortest diameter in mm. Changes in tumor Volumes (Δ volumes) for each treated (T) and control (C) group are calculated, by subtracting the mean tumor volume on the first day of treatment (starting day) from the mean tumor volume of on the specified observation day. These values are used to calculate a percentage growth (% T/C) using the formula:

% $T/C = (\Delta T/\Delta C) \times 100$ where $\Delta T > 0$ or $= (\Delta T/\Delta Ti) \times 100$ where $\Delta T < 0,$ where Ti is the mean tumor volume at the start of treatment.

Percentage tumor growth inhibition was calculated using the formula:

Percentage Tumor growth inhibition = 100 − % T/C.

Tumor regressions are defined as partial if the tumor volume decreases to 50% or less of the tumor volume at the start of the treatment without dropping below to 63 mm$^3$. Complete regression is defined if the tumor volume drops to below measurable limits (<63 mm 3)

The percentage body weight change in comparison to starting day body weight of each animal was calculated using the formula:

Percentage Body weight change=[(Body weight on specified observation day−Body weight on starting day)/Body weight on starting day]×100.

The other parameter observed was mortality.

The results of the tests are shown in Table 4, where the tumor growth inhibition and the mortality is shown for each of the two test compounds and for the control.

TABLE 4

Effect of 5(S)-CPT and 5(RS)-CPT on tumor growth inhibition and mortality of nude mice having NCI-H460 (human small cell lung carcinoma) xenografts.

| Compound | Dose (mg/kg) | % Tumor Growth Inhibition | Mortality |
|---|---|---|---|
| 5(S)-CPT | 2 | 68 | 0/5 |
|  | 4 | 76 | 0/5 |
| 5(RS)-CPT | 2 | 60 | 0/5 |
|  | 4 | 64 | 0/5 |

The data from this test showed that 5(S)-CPT demonstrated better in vivo activity against NCI-H460 (human small cell lung carcinoma) xenografts in nude mice than the diastereoisomeric mixture 5(RS)-CPT. As shown in Table 4, the administration of 5(S)-CPT led to unexpectedly superior inhibition of tumor growth in comparison with the administration of 5(RS)-CPT at identical doses (68% vs 60% at 2 mg/kg, and 76% vs 64% at 4 mg/kg) without an increase in mortality.

EXAMPLE 5

This example illustrates the efficacy of 5(S)-CPT versus 5(R)-CPT in inhibiting in vitro cell proliferation in a Sulphorhodamine B (SRB) assay Samples of 5(S)-CPT and 5(R)-CPT were provided as described in Example 3.

Protocol for In Vitro Cell Growth Assay:

Cell proliferation was evaluated by Sulphorhodamine B (SRB) assay where the amount of dye bound to the cells after staining gives a measure of cell growth. Refer to: *JNCI*, vol 83, No. 11, Jun. 5, 1991, which is incorporated herein by reference.

Briefly, cells (34 human cancer cell lines represented by bladder, breast, CNS, colon, epidermoid, lung, ovarian, melanoma, prostate, renal and uterine cancers) were seeded on a 96-well cell culture plates at a concentration of 10000 cells per well and incubated at 37° C. in a $CO_2$ incubator. Twenty-four hours later, cells were treated with different concentrations of the test compound dissolved in DMSO to a final concentration of 0.05% in the culture medium and exposed for 48 hours. Cells were fixed by adding ice-cold 50% trichloroacetic acid (TCA) and incubating for 1 hour at 4° C. The plates were washed with distilled water, air dried and stained with SRB solution (0.4% wt/vol in 1% Acetic acid) for 10 minutes at room temperature. Unbound SRB was removed by washing thoroughly with 1% acetic acid and the plates were air-dried. The bound SRB stain was solubilized with 10 mM Tris buffer, and the optical densities were read on a spectrophotometric plate reader at a single wavelength of 515 nm. At the time of drug addition separate reference plate for cell growth at time 0 hours (the time at which drugs were added) was also terminated as described above. From the optical densities the percentage growths were calculated using the following formulae:

If $T$ is greater than or equal to $T_0$, percentage growth=$100\times[(T-T_0)/(C-T_0)]$ and if $T$ is less than $T_0$, percentage growth=$100\times[(T-T_0)/T_0]$, Where T is optical density of test, C is the optical density of control and $T_0$ is the optical density at time zero.

From the percentage growth data a dose response curve was generated and $GI_{50}$ values were interpolated from the growth curves. Table 5 shows the results.

TABLE 5

$GI_{50}$ values for 5(S)-CPT versus 5(R)-CPT.

| Compound | $GI_{50}(\mu M)$ |
|---|---|
| 5(S)-CPT | 5.0 |
| 5(R)-CPT | 14.6 |

The results of this test showed that the 5(S)-CPT diastereoisomers was almost three times more active than the 5(R)-CPT diastereoisomers against cell proliferation in the test.

EXAMPLE 6

This example illustrates the efficacy of 5(S)-CPT in several osteosarcoma tumor models.

Samples of 5(S)-CPT and 5(RS)-CPT were provided as described in Example 3. The protocol for the test is found in *Cancer Res.*, Oct. 15:64(2):7491-9 (2004), and in *Clin. Cancer Res.*, Nov. 15:9(15):5442-53 (2003).

All mice bearing subcutaneous ("sc") tumors measuring approximately 0.2-1 cm in diameter were treated with a test compound by oral gavage using [(d×5)2]3 schedule. Tumor diameters were measured every 7 days using Vernier calipers and tumor volumes were calculated, assuming tumors to be spherical, using the formula $[\pi/6)\times d^3]$, where d is the mean diameter. The tumor response to the test compound was defined as follows: For individual tumors, PR was defined as a volume regression >50%, but with measurable tumor at all times. CR was defined as disappearance of measurable tumor mass at some point within 12 weeks after initiation of therapy. Maintained CR is defined as no tumor re-growth within a 12-week study time frame. This time point was chosen because all studies lasted at least 12 weeks. Mice that died before the end of the 12-week study time, and prior to achieving a response, were considered as failures for tumor response. The results (dose of 28 mg/kg) are presented in Table 6.

TABLE 6

Efficacy of 5(S)-CPT versus 5(RS)-CPT in mouse tumor regression models.

| Xenograft | 5(S)-CPT | 5(RS)-CPT |
|---|---|---|
| Osteosarcoma-29 | 6+ | 5+ |
| Osteosarcoma-17 | 6+ | 4+ |
| Osteosarcoma-2 | 6+ | 5+ |
| Osteosarcoma-32 | 6+ | 3+ |

6+: Maintained Complete Regression
5+: Complete Regression
4+: Partial Regression
3+: Stable Disease As shown by the date of Table 6, administration of 5(S)-CPT led to unexpectedly superior results in comparison with the administration of 5(RS)-CPT, as indicated by maintained complete regression (6+) achieved with 5(S)-CPT in all four xenograft lines.

The data provided in Examples 5 and 6 illustrate that 5(S)-CPT has unexpectedly superior activity/potency profile in several test models. Furthermore, while 5(S)-CPT is substantially more potent than 5(R)-CPT, the increase in potency is unexpectedly not accompanied by a corresponding increase in toxicity.

EXAMPLE 7

This example shows the human bone marrow toxicity of 5(S)-CPT versus 5(R)-CPT.

Samples of 5(S)-CPT and 5(R)-CPT were provided as described in Example 3.

Protocol for Human Bone Marrow Assay:

Methocult™ GF (Cat No: H4534, Poietics, Biowhittakar, USA) medium comprising Methycellulose in Iscove's MDM, Fetal bovine serum, Bovine serum albumin, 2-Mercaptoethanol, L-Glutamine, rhStem cell factor, rhGM-CSF and rhIL-3 was used for the assay. Human bone marrow mononuclear cells (Cat No. 2M-125C, Poietics, Biowhittakar, USA) were mixed with Methocult™ GF and the cell density was adjusted to $3 \times 10^5$ cells/ml. From this preparation, 500 µL aliquots were made and 2.5 µL of 20× drug solution or vehicle was added to each aliquot and mixed thoroughly. 100 µL of clonogenic medium was plated into each well and the plates were allowed to gel at 4° C. for 15 minutes. Plates were incubated at 37° C. in a fully humidified atmosphere of 5% $CO_2$ in an incubator for 14 days. CFU-GM colonies were counted under an inverted microscope as aggregates of 50 cells or more. The percentage colony inhibition was calculated using the following formula:

100−[(number of colonies in drug treated wells/Number of colonies in control wells)×100].

The in vitro potency of the two diastereomers (5(S)-CPT and 5(R)-CPT respectively) against cancer cell lines had been compared with their in vitro toxicity in healthy cells. Table 7 presents the results of the bone marrow toxicity comparison study in human cells.

TABLE 7

$GI_{90}$ values for 5(S)-CPT and 5(R)-CPT for human bone marrow cells in vitro.

| Compound | $GI_{90}(\mu M)$ |
|---|---|
| 5(S)-CPT | 0.69 |
| 5(R)-CPT | 0.89 |

With reference to the date shown in Table 5, it can be seen that while 5(S)-CPT is unexpectedly almost 3 times more potent than 5(R)-CPT against 34 human cancer cell lines representing bladder, breast, CNS, colon, epidermoid, lung, ovarian, melanoma, prostate, renal and uterine cancers, the toxicities of both diastereomers are comparable. In fact, if the safety margin is estimated as the ratio of $GI_{90}$ for human cell toxicity to $GI_{50}$ for anticancer activity, as shown in Table 8, it is apparent that 5(S)-CPT is unexpectedly superior to 5(R)-CPT and 5(RS)-CPT as a pharmaceutical compound for treatment of cancer. In other words, the 5(S)-CPT compound has increased efficacy with respect to treatment of cancer in comparison with 5(R)-CPT and the mixture of 5(S)-CPT and 5(R)-CPT. In fact, it is unexpectedly important to minimize the amount of the 5(R)-CPT present in the 5(S)-CPT to be given to patients.

TABLE 8

Ratio of $GI_{90}$ for human cell toxicity to $GI_{50}$ for anticancer activity for 5(S)-CPT and 5(R)-CPT

| Compound | Safety Margin ($GI_{90}/GI_{50}$) |
|---|---|
| 5(S)-CPT | 0.14 |
| 5(R)-CPT | 0.06 |

EXAMPLE 8

This example shows the effect of the presence of 5(R)-CPT on the bioavailability of 5(S)-CPT in rats and mice.

Samples of 5(S)-CPT and 5(RS)-CPT were provided as described in Example 3.

Bioavailability in Male Wistar Rats:

5(S)-CPT (2.5 mg/kg) and 5(RS)-CPT (5 mg/kg, including 2.5 mg/kg of 5(S)-CPT in the mixture) were been administered to male Wistar Rats to evaluate oral pharmacokinetics.

Male Wistar rats, 6-8 weeks of age and weighing between 205 and 218 g were divided into groups of four rats. The oral pharmacokinetics test was carried out in overnight fasted condition and intravenous pharmacokinetics was carried out in fed condition. The test drugs were administered as a solution by oral gavage or lateral tail vein injection. Sparse blood samples of about 250 microliters were collected from retro-orbital plexus at designated time points into microcentrifuge tubes containing 25 microliters of EDTA. Plasma was separated by centrifuging blood at 12,800 rpm for 2 min and refrigerated until analysis.

Samples were tested for the presence of the test drug as follows. An aliquot of 100 µl plasma (stored at 8° C.) was precipitated with 400 µl of cold methanol for the estimation of total (lactone+carboxylate). Following mixing for 2 min. and centrifugation for 4 min. at 12,800 rpm, clear supernatant was separated into a 300 µl auto-sampler vial and 20 µl of this mixture was injected onto an analytical column for HPLC analysis. Concentrations of the test drug were calculated from the linearity plotted by spiking known concentrations of the test drug in blank rat plasma. The pharmacokinetics of the test drug was calculated using non-compartmental analysis.

The results of the study are presented in Table 9.

TABLE 9

Oral pharmacokinetic parameters of 5(S)-CPT in male Wistar rats.

| Compound | Dose | AUC(o-t) µM*h |
|---|---|---|
| 5(S)-CPT | 5 mg/kg | 5.76 |
| 5(RS)-CPT | 5 mg/kg (2.5 mg/kg 5(S)-CPT + 2.5 mg/kg 5(R)-CPT) | 5.08 |
| Contribution of 5(S)-CPT in 5(RS)-CPT | 2.5 mg/kg | 1.21 |

Bioavailability in Swiss Albino Mice:

5(S)-CPT (2.5 mg/kg) and 5(RS)-CPT (5 mg/kg, including 2.5 mg/kg of 5(S)-CPT in the mixture) were been administered to Swiss Albino mice to evaluate oral pharmacokinetics.

Swiss Albino mice, 3-6 weeks of age and weighing between 28-34 g were used in the study. Twelve mice were used per study. The oral pharmacokinetics test was carried out in overnight fasted condition and intravenous pharmacokinetics was carried out in fed condition. The test drugs were administered as a solution by oral gavage or lateral tail vein injection. Sparse blood samples of about 250 microliters were collected from retro-orbital plexus at designated time points into microcentrifuge tubes containing 25 microliters of EDTA. Plasma was separated by centrifuging blood at 12,800 rpm for 2 min and refrigerated until analysis.

Samples were tested for the presence of the test drug as follows. An aliquot of 100 µl plasma (stored at 8° C.) was precipitated with 400 µl of cold methanol for the estimation of total (lactone+carboxylate). Following mixing for 2 min. and centrifugation for 4 min. at 12,800 rpm, clear supernatant was separated into a 300 µl auto-sampler vial and 20 µl of this mixture was injected onto an analytical column for HPLC analysis. Concentrations of the test drug were calculated from the linearity plotted by spiking known concentrations of the test drug in blank rat plasma. The pharmacokinetics of the test drug was calculated using non-compartmental analysis. The results of the study are presented in Table 10.

TABLE 10

Oral pharmacokinetic parameters of 5(S)-CPT in Swiss Albino mice.

| Compound | Dose | AUC(o-t) µM*h |
|---|---|---|
| 5(S)-CPT | 5 mg/kg | 5.18 |
| 5(RS)-CPT | 5 mg/kg (2.5 mg/kg 5(S)-CPT + 2.5 mg/kg 5(R)-CPT) | 5.20 |
| Contribution of 5(S)-CPT in 5(RS)-CPT | 2.5 mg/kg | 1.10 |

With reference to Tables 9 and 10, the "contribution of 5(S)-CPT is the Area Under Curve ("AUC") that can be attributed to the 5(S)-CPT in the 5(RS)-CPT diastereomeric mixture. As can be seen from Tables 9 and 10, the presence of 5(R)-CPT unexpectedly decreases bioavailability of the desired 5(S)-CPT diastereomer. Moreover, it is believed that such unexpected decrease in bioavailability for the desired diastereomers would be observed in human patients. On the basis of the above, minimization of the amount of the 5(R)-CPT in 5(S)-CPT is highly desirable.

EXAMPLE 9

This example illustrates the efficacy of 5(S)-CPT versus 5(R)-CPT and 5(RS)-CPT against BCRP mutant and Breast cancer resistance protein (BCRP) over expressing Saos-2 cells.

Samples of 5(S)-CPT, 5(R)-CPT and 5(RS)-CPT were provided as described in Example 3.

Protocol for Breast Cancer Resistance Protein (BCRP) Assay:

The anticancer effect of 5(S)-CPT & 5(R)-CPT were evaluated versus the diastereoisomeric mixture 5(RS)-CPT on Saos-2 cells over expressing functional BCRP#4 and non-functional BCRP mut#10. The human osteosarcoma cell line, Saos-2, was obtained from ATCC (American Type Culture Collection, Cat#HTB-85, Manassas, Va.) and were maintained in DMEM containing 10% fetal bovine serum, 1% penicillin/streptomycin, and 2 mM glutamine. Saos-2 cells were transfected with either BCRP#4 to over express functional BCRP or BCRP#10 to over express non-functional BCRP transporter. The cells were plated in 96-well plates at a density of 1000 cells per each well in a 0.1 ml of medium and allowed to attach overnight. The next morning the medium was gently aspirated and serial dilutions of the compounds to be tested were added. The cells were incubated at 37° C. in a 5% $CO_2$ incubator. After 6 days of exposure to the test drugs, 10 µl of Alamar blue was added aseptically to each well and the plates were returned to the incubator for 6 hr. The amount of the fluorescent dye produced was measured on a Cytofluor 2300(Millipore, Bedford, Mass.) using an excitation wavelength of 530 nm and emission wavelength of 590 nm. The relative fluorescence units obtained were used to calculate the percentage growth at each concentration in relation to the untreated control values. From the percentage growth values the $IC_{50}$ (inhibitory concentration required to inhibit the cell growth by 50% compared to control cells growth) values were derived. The resulting $IC_{50}$ values are presented in Table 11.

TABLE 11

$IC_{50}$ values for 5(S)-CPT, 5(R)-CPT and 5(RS)-CPT against BCRP mutant and Breast cancer resistance protein (BCRP) over expressing Saos-2 cells.

| | $IC_{50}$ (nM) | |
|---|---|---|
| Drug | BCRP mut#10 | BCRP#4 |
| 5(RS)-CPT | 387 | 1256 |
| 5(S)-CPT | 213 | 788 |
| 5(R)-CPT | 1299 | >2000 |

As shown in Table 11, 5(S)-CPT is superior to 5(R)-CPT and 5(RS)-CPT in terms of its cytotoxic activity on BCRP mutant as well as BCRP over expressing Saos-2 cells. These results indicate that the rank order of cytotoxicity on both BCRP mut#10 and BCRP#4 was 5(S)-CPT>5(RS)-CPT>5(R)-CPT. 5(S)-CPT was ~6 and >2.5 fold more cytotoxic than 5(R)-CPT on BCRP mut#10 and BCRP#4 over expressing Saos-2 cells, respectively.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results obtained.

As various changes could be made in the above methods and compositions by those of ordinary skill in the art without departing from the scope of the invention, it is intended that all matter contained in the above description and shown in the accompanying drawings shall be interpreted as illustrative and not in a limiting sense. In addition it should be understood that aspects of the various embodiments may be interchanged both in whole or in part.

What is claimed is:

1. A crystalline form of 5(S)-(2'-hydroxyethoxy)-20(S)-camptothecin, having the structure

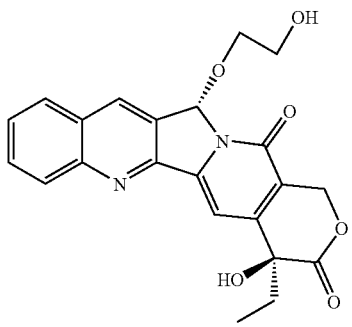

and further comprising an X-ray powder diffraction pattern comprising one or more peak intensities expressed in degrees 2θ that are selected from the group consisting of 7.2±0.1, 9.4±0.1, 11.02±0.1, 12.00±0.1, 14.54±0.1, 15.2±0.1, 18.92±0.1, 21.86±0.1, 22.74±0.1 and 26.42±0.1.

2. The crystalline 5(S)-(2'-hydroxyethoxy)-20(S)-camptothecin according to claim 1, having crystals in monoclinic space group P2$_1$ with unit cell parameters a=6.308(1)Å, b=15.924(3) Å, c=18.771(4) Å, β95.519(5) Å; V=1876.8(7) Å$^3$ and Z=4, as measured by a single crystal diffractometer using graphite monochromatic MoKa radiation (λ=0.7107 Å) on a CCD area-detector.

3. The crystalline 5(S)-(2'-hydroxyethoxy)-20(S)-camptothecin according to claim 1, having a single melting endotherm peak between about 234° C. and 238° C. as measured by differential scanning calorimetry.

4. The crystalline 5(S)-(2'-hydroxyethoxy)-20(S)-camptothecin according to claim 1, which is anhydrous.

5. The crystalline 5(S)-(2'-hydroxyethoxy)-20(S)-camptothecin according to claim 1, having an overall phase purity of over 97%.

6. The crystalline 5(S)-(2'-hydroxyethoxy)-20(S)-camptothecin according to claim 1, which is substantially free of 5(R)-(2'-hydroxyethoxy)-20(S)-camptothecin.

7. The crystalline 5(S)-(2'-hydroxyethoxy)-20(S)-camptothecin according to claim 1, having an X-ray powder diffraction peak at 7.2±0.1 degrees 2θ.

8. The crystalline 5(S)-(2'-hydroxyethoxy)-20(S)-camptothecin according to claim 7, further having at least one additional X-ray powder diffraction peak selected from the group consisting of 9.4±0.1, 11.02±0.1, 12.00±0.1, 14.54±0.1, 15.20±0.1, and 18.92±0.1 degrees 2θ.

9. The crystalline 5(S)-(2'-hydroxyethoxy)-20(S)-camptothecin according to claim 1, further having an FT-IR spectrum that comprises at least one absorption band selected from the group consisting of 3271±2, 1743±2, 1669±2, 1607±2, 1225±2, 1158±2, 1043±2 and 992±2 cm$^{-1}$.

10. The crystalline 5(S)-(2'-hydroxyethoxy)-20(S)-camptothecin according to claim 1, further having an FT-IR spectrum that comprises an absorption band at 1743±2 cm$^{-1}$.

11. The crystalline 5(S)-(2'-hydroxyethoxy)-20(S)-camptothecin according to claim 10, and having an FT-IR spectrum that further comprises at least one absorption band selected from the group consisting of 3271±2, 1669±2, 1607±2, 1225±2, 1158±2, 1043±2 and 992±2 cm$^{-1}$.

12. The crystalline 5(S)-(2'-hydroxyethoxy)-20(S)-camptothecin according to claim 1, having an X-ray diffraction pattern comprising a diffraction peak at 7.2±0.1 degrees 2θ, and an FT-IR spectrum comprising an absorption band at 1743±2 cm$^{-1}$.

13. The crystalline 5(S)-(2'-hydroxyethoxy)-20(S)-camptothecin according to claim 1, having an X-ray diffraction pattern comprising a diffraction peak at 7.2±0.1 degrees 2θ, and an FT-IR spectrum comprising absorption bands at 3271±2 and 1743±2 cm$^{-1}$.

14. The crystalline 5(S)-(2'-hydroxyethoxy)-20(S)-camptothecin according to claim 1, having an X-ray powder diffraction pattern comprising diffraction peaks at 7.2±0.1 and 9.4±0.1 degrees 2θ and an FT-IR spectrum comprising an absorption band at 1743±2 cm$^{-1}$.

15. The crystalline 5(S)-(2'-hydroxyethoxy)-20(S)-camptothecin according to claim 1, having an X-ray powder diffraction pattern comprising diffraction peaks at 7.2±0.1 and 9.4±0.1 degrees 2θ, and an FT-IR spectrum comprising absorption bands at 3271±2 and 1743±2 cm$^{-1}$.

16. The crystalline 5(S)-(2'-hydroxyethoxy)-20(S)-camptothecin according to claim 1, having an X-ray powder diffraction pattern comprising diffraction peaks at 7.2±0.1, 9.4±0.1, 11.02±0.1; 12.00±0.1; 14.54±0.1; 15.20±0.1; and 18.92±0.1 degrees 2θ, and an FT-IR spectrum comprising absorption bands at 3271±2, 1743±2, 1669±2, 1607±2, 1225±2, 1158±2, 1043±2 and 992±2 cm$^{-1}$.

17. The crystalline 5(S)-(2'-hydroxyethoxy)-20(S)-camptothecin according to claim 1, having an X-ray powder diffraction pattern comprising diffraction peaks at 7.2±0.1, 9.4±0.1, 11.02±0.1; 12.00±0.1; 14.54±0.1; 15.20±0.1; and 18.92±0.1 degrees 2θ, and a melting point in a range of about 234° C. to about 238° C.

18. The crystalline form of 5(S)-(2'-hydroxyethoxy)-20(S)-camptothecin according to claim 1, comprising the camptothecin dimer of formula V as an impurity (V)

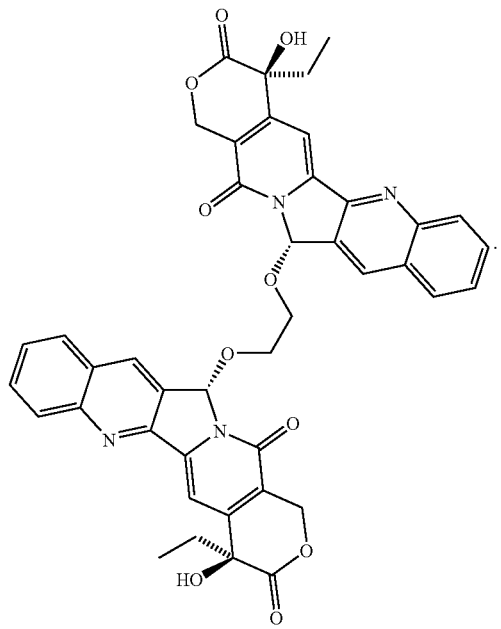

19. The crystalline form of 5(S)-(2'-hydroxyethoxy)-20(S)-camptothecin according to claim 18, comprising the camptothecin dimer in an amount less than about 1.5% w/w.

20. The crystalline form of 5(S)-(2'-hydroxyethoxy)-20(S)-camptothecin according to claim 18, comprising the camptothecin dimer in an amount less than about 0.8% w/w.

21. The crystalline form of 5(S)-(2'-hydroxyethoxy)-20(S)-camptothecin according to claim 18, comprising the camptothecin dimer in an amount less than about 0.5% w/w.

22. The crystalline form of 5(S)-(2'-hydroxyethoxy)-20(S)-camptothecin according to claim 18, comprising the camptothecin dimer in an amount less than about 0.1% w/w.

23. A pharmaceutical composition comprising the crystalline 5(S)-(2'-hydroxyethoxy)-20(S)-camptothecin as described in claim 1 and a pharmaceutically acceptable carrier.

24. The pharmaceutical composition according to claim 23, wherein a single dose of the composition for an adult human comprises from about 5 mg to about 25 mg of 5(S)-(2'-hydroxyethoxy)-20(S)-camptothecin.

25. A method for the preparation of a pharmaceutical composition, the method comprising intermixing the crystalline 5(S)-(2'-hydroxyethoxy)-20(S)-camptothecin described in claim 1 with a pharmaceutically acceptable carrier.

26. A method of making the crystalline 5(S)-(2'-hydroxyethoxy)-20(S)-camptothecin described in claim 1, the method comprising the steps:
   a) intermixing 5(RS)-(2'-hydroxyethoxy)-20(S)-camptothecin with a solvent selected from n-butanol or tetrahydrofuran;
   b) refluxing the mixture for a period of from about 1 to about 4 hours;
   c) cooling the mixture to a temperature of from about 40° C. to about 50° C.; and
   d) separating solid 5(S)-(2'-hydroxyethoxy)-20(S)-camptothecin from the mixture.

27. The method according to claim 26, further comprising the steps:
   e) washing the solid 5(S)-(2'-hydroxyethoxy)-20(S)-camptothecin with a solvent selected from n-butanol or tetrahydrofuran; and
   d) drying the solid 5(S)-(2'-hydroxyethoxy)-20(S)-camptothecin to yield 5(S)-(2'-hydroxyethoxy)-20(S)-camptothecin that is substantially free of 5(R)-(2'-hydroxyethoxy)-20(S)-camptothecin.

28. A method of treating cancer in a subject, the method comprising administering to the subject an effective amount of the crystalline 5(S)-(2'-hydroxyethoxy)-20(S)-camptothecin described in claim 1, and wherein the cancer is one that is selected from the group consisting of ovarian cancer, osteosarcoma, small cell lung cancer, non-small cell luna cancer, central nervous system (CNS) cancer, renal cancer, bladder cancer, breast cancer, epidermoid cancer, lung cancer, melanoma, prostate cancer, uterine cancer, and colon cancer.

29. The method according to claim 28, wherein the subject is a mammal.

30. The method according to claim 29, wherein the subject is a human.

31. The method according to claim 29, wherein the crystalline 5(S)-(2'-hydroxyethoxy)-20(S)-camptothecin is administered to the subject orally.

32. The method according to claim 29, wherein the cancer is one that is selected from the group consisting of colon cancer, ovarian cancer and osteosarcoma.

33. The method according to claim 29, wherein the cancer is one that is selected from the group consisting of osteosarcoma, and colon cancer.

34. The method according to claim 29, wherein the cancer is one that is selected from the group consisting of bladder, breast, CNS, colon, epidermoid, lung, ovarian, melanoma, prostate, renal and uterine cancers.

35. The method according to claim 29, wherein the crystalline 5(S)-(2'-hydroxyethoxy)-20(S)-camptothecin is administered to the subject in an amount of from about 0.1 to about 5 mg/kg/day.

36. The method according to claim 29, wherein the crystalline 5(S)-(2'-hydroxyethoxy)-20(S)-camptothecin is administered to the subject in an amount of from about 0.2 to about 3 mg/kg/day.

\* \* \* \* \*

UNITED STATES PATENT AND TRADEMARK OFFICE
CERTIFICATE OF CORRECTION

PATENT NO. : 7,601,732 B2 Page 1 of 1
APPLICATION NO. : 11/753392
DATED : October 13, 2009
INVENTOR(S) : Venkateswarlu Akella It is certified that error appears in the above-identified patent and that said Letters Patent is hereby corrected as shown below:

Title Page item 54 and Col. 1
Replace the number "-2" with the number -- -2' -- in the title of the issued Patent.

Replace the term "oleaginous" with the term -- olagenous -- in Column 14, line 61, of the issued Patent.

Replace the term "(A)" with the symbol -- (Δ) -- in Column 20, line 27, of the issued Patent.

Signed and Sealed this

Twelfth Day of October, 2010

David J. Kappos
*Director of the United States Patent and Trademark Office*